United States Patent [19]

Lyte

[11] Patent Number: 5,629,349
[45] Date of Patent: May 13, 1997

[54] COMPOUNDS FOR MODULATING GROWTH OF INFECTIOUS AGENTS

[75] Inventor: Mark Lyte, Mankato, Minn.

[73] Assignee: Minnesota State University System Through Its Mankato State University Agency, Mankato, Minn.

[21] Appl. No.: 266,805

[22] Filed: Jun. 27, 1994

Related U.S. Application Data

[63] Continuation of Ser. No. 847,196, Mar. 6, 1992, abandoned, which is a continuation-in-part of Ser. No. 753,709, Sep. 3, 1991, abandoned, which is a continuation-in-part of Ser. No. 730,485, Jul. 16, 1991, abandoned.

[51] Int. Cl.$^6$ .................... A61K 31/135; A01N 33/10
[52] U.S. Cl. ............... 514/653; 435/29; 435/41; 435/253.6; 514/224.8; 514/727
[58] Field of Search .................. 435/29, 41, 253.6; 514/224.8, 727, 653

[56] References Cited

U.S. PATENT DOCUMENTS 4,689,332  8/1987  McLaughlin.

OTHER PUBLICATIONS

"Plasme Catecholamines During *E. coli* Bactermia in Conscious Rats", Jones, Stephen B., et al, *America Journal of Physiology*, 254:R470–477, 1988.
"High Concentration of (–) Noradrenaline in *Portulaca oleracea* L.", *Nature*, Sep. 9, 1961, vol. 191, p. 108.
"A Note on the Presdence of Noradrenaline and 5–Hydroxy–tryptamine in Plantain (*Musa Sapientum, Var. paradisiaca*)", Foy, J.M., et al, From the Department of Pharmacy, Nigerian College of Technology, Ibadan, West Nigeria, pp. 360–364.
"Physiologically Active Amines in Common Fruits and Vegetables", Udenfriend, Sidney, et al, *Archives of Biochemistry and Biophysics*, 85, 4870490 (1959).
"Serotonin, Norepinephrine, and Related Compounds in Bananas", *Science*, vol. 127 Mar. 1958, pp. 648–650.
"Bacteraemic Shock", The Lancet, Feb. 23, 1974, pp. 296–297.
"The Neurotransmitter Noradrenaline and Its Receptors", Surprenant, Annmarie, The Neurosciences, vol. 1, 1989: pp. 125–136.
"Methods in Neurotransmitter Receptor Analysis", Yamamura, Henry I., et al.

"Methods for Receptor Binding", Bylund, David B., et al.
"Stress and Immunologic Competence: Studies in Animals", Monjan, Andrew A.
"The Inhibitory Effect of *coli*–Endotoxin on Alpha–Adrenergic Receptor Functions in the Lower Urinary Tract", Nergardh, Arne, et al, *Scand. J. Urol. Nephrol*, 11:219–224, 1977.
"Distributed Adrenergic Regulation of Coronary Flow in the Guinea Pig Heart After *Bordetella pertussis* and Endotoxin", Heuven–Noisen, D. Van, et al. *Agents and Actions*, vol. 17, 3/4 (1985).
"Endogenous Opioid Systems Are Present and Relate the Growth of Bacteria", Society for Neuroscience Abstracts, vol. 16, Part 2, 20th Annual Meeting, St. Louis, Missouri, Oct. 28–Nov. 2, 1990.
"Naltrexone Modulates Growth in Infant Rats", Zagon, Ian S., et al, *Life Sciences*, vol. 33, pp. 2449–2454.
Dyer et al, Chem. Abst., vol. 102 (1985), pp. 179, 661r.
Moger et al, Chem. Abst., vol. 97 (1982), pp. 157,029s.
Khotimchenko, Chem. Abst., vol. 97 (1982), p. 36514n.
Sukmanskii et al, Chem. Abst., vol. 101 (1984), p. 144,669b.
Kurnatowski, Chem. Abst., vol. 102 (1985), p. 146,020c.
Magyar et al, Chem. Abst., vol. 102 (1985), p. 137,803g.
Delitheos et al, Chem. Abst. vol. 97 (1982), p. 212,567t.
Qualliotine et al, Chem. Abst., vol. 77 (1972), p. 160,633b.
Denisenko et al, Chem. Abst., vol. 81 (1974), p. 45,312s.

*Primary Examiner*—Herbert J. Lilling
*Attorney, Agent, or Firm*—Haugen and Nikolai, P.A.

[57] ABSTRACT

A method for modulating both in vivo and/or in vitro bacterial growth by administration of neurochemicals is disclosed. This method involves the recognition of a novel receptor for these compounds and includes the steps of: assessing need to apply a neurotransmitter chemical based upon the nature of the living organism, determining an amount of neurotransmitter chemical required to produce an effect upon the rate of proliferation, applying the neurotransmitter chemical to the living organism, assessing efficacy of this application in reducing or enhancing the rate, and repeating these steps intermittently to monitor the actual rate of proliferation, whether accelerated or depressed. A method is further disclosed wherein the subject neurotransmitter chemical, such as a catecholamine, is added to a basal culture medium for the purpose of augmenting (or suppressing) growth. This step is useful for the commercial production of organisms such as bacteria. It is further useful for the increased production of commercially useful byproducts of this augmented growth, such as glucose or ethanol.

2 Claims, 16 Drawing Sheets

TABLE 1

| MICROBE | CFU | CATECHOLAMINE (DPM) | | | | | |
|---|---|---|---|---|---|---|---|
| | | 0 | NE | EPI | DOPA | MHPG | NOR |
| YERSINIA ENTEROCOLITICA | 80 | 722 | 54342 | 856 | 6623 | 853 | 866 |
| ESCHERICHIA COLI | 15 | 258 | 24629 | 1563 | 4354 | 1105 | 632 |
| ESCHERICHIA COLI | 1500 | 135349 | 243531 | 226365 | 255121 | 183496 | 95081 |

FIG. 21

TABLE 2

| CFU | COMPOUND (DPM) | | | | | |
|---|---|---|---|---|---|---|
| | 0 | NE | OCI | (-)ISO | (+)ISO | EPH |
| 130 | 150 | 29243 | 159 | 146 | 183 | 297 |

FIG. 22

COMPOUNDS FOR MODULATING GROWTH OF INFECTIOUS AGENTS

The findings reported herein were funded by the National Institute of Health, under grant MH-45246, and accordingly the United States Government has acquired ownership of certain rights in the invention.

CROSS-REFERENCE TO RELATED APPLICATION

This is a continuation of application Ser. No. 07/847,196, filed Mar. 6, 1992 (now abandoned), which is itself a continuation-in-part of application Ser. No. 07/753,709, filed Sep. 3, 1991 (now abandoned), which is itself a continuation-in-part of application Ser. No. 07/730,485, filed Jul. 16, 1991 (now abandoned).

BACKGROUND OF THE INVENTION

I. Field of the Invention

This invention relates generally to a method of modulating the proliferation of microorganisms or other infectious vectors and, more particularly, to a method of introducing a neurochemical to augment, repress or otherwise affect the growth of Gram-reactive organisms. The process involves the introduction (or application) of effective amounts of a group of neurochemicals known as the catecholamines. Each microorganism tested has been shown to have specific requirements for one or more of the subject catecholamines. Depending on the catecholamine being employed, suppression or enhancement of growth may be effected. Furthermore, growth regulation can be effected in vivo and/or in vitro. The characterization of the receptor through which the catecholamine binds to the cell or cellular components as novel, enables further control of cell growth by the application of either receptor agonists or antagonists specific for this novel receptor.

II. Discussion of the Prior Art

Sepsis is the generally febrile pathologic state resulting from the presence of microorganisms or their poisonous products in the blood stream particularly in humans or other mammals. It occurs when spreading infectious agents are not successfully arrested within the lymph nodes, and thus directly invade venous channels. Although it is not uncommon to have periodic invasions of bacteria into the blood stream, called bacteremia, these outbursts are normally handled quickly and effectively by macrophages circulating in the blood. However, in some circumstances, such large numbers of bacteria may be involved in the invasion that the macrophages are overwhelmed and under-effective, resulting in the symptoms of fever, chills, general malaise and lethargy known as septicemia. In aggravated cases, it is possible that organisms reach such a high population within the circulation that they circulate in clumps. Under these conditions, it is possible that these circulating clumps may lodge within organs and produce large numbers of microabscesses, a situation which is called septicoyemia.

Traditional treatment of sepsis, septicemia, or septicoyemia is performed using antimicrobial agents, typically in conjunction with the use of vasoactive drugs such as norepinephrine and dopamine. These antimicrobial agents are typically designed to affect bacterial wall structure or bacterial metabolic processes. Such agents may be particularly targeted at a specific metabolic process or cellular receptor. However, despite this specificity, conventional antimicrobial therapy is unsuccessful in a large number of cases. In particular, it has been documented that up to 60% of all patients diagnosed with sepsis eventually succumb to the condition. Thus, despite the great strides forward, there remains great need for more specific and more effective antimicrobial agents or treatment protocols.

The primary role for the use of vasoactive drugs in septic conditions has been the restoration of normal hemodynamics. A typical clinical picture involving sepsis is the patient who fails to respond to traditional treatment or who undergoes intensive antibiotic therapy and apparent resolution of sepsis, with improvement in condition two to three days post admission to hospital. However, nearly 40% of patients relapse on the third to fourth day of treatment, with death ensuing rapidly thereafter. My recent data indicates that the use of catecholamines (such as norepinephrine and dopamine) as the preferred vasoactive agents may, in fact, be an essential factor contributing to the worsening clinical condition. My data indicates that administration of catecholamines to patients in these conditions results in providing some bacteria with a potent growth stimulus that permits rapid proliferation bacteria and eventual death of the patient, even in the face of appropriate antibiotic therapy.

Catecholamines in humans are a class of hormones that evoke a response by activation of adenyl cyclase. These compounds are targeted to specific hormone receptors in mammals and produce varied responses, depending upon the nature of the target tissue. The majority of catecholamines evoke their characteristic response by influencing the activity of pre-existing cellular enzyme systems. Thus, the response evoked may be almost instantaneous, such as in the case of neurotransmitters including norepinephrine and epinephrine. Norepinephrine, epinephrine and dopamine are the characteristic hormones of the mammalian sympathetic nervous system. All are amine derivatives of the catechol nucleus (dihydroxybenzene). These compounds have clearly identified peripheral effects. Classic feedback inhibition processes control the production of these compounds, in which the rate limiting step in the pathway is hydroxylation of the amino acid precursor tyrosine to form dihydroxyphenylalanine (dopa). In mammals, synthesis of catecholamines is a unique feature of sympathetic nervous tissue. However, in certain disease states, hormone producing tumors may release catecholamines directly into the circulation and, thus, manifest peripheral effects of these compounds as a result of plasma concentration instead of local tissue concentration. Other states, such as stress, are also classic activators of the production of catecholamines concomitant with the presumed suppression of the immune system. Otherwise, most manifest a non-circulatory effect.

Jones, et al., among others, have noted a severalfold increase in plasma norepinephrine and epinephrine levels during bacteremia. This increase has been attributed to activation of the adrenal medulla and peripheral sympathetic fibers. They suggest that plasma catecholamines may be an indicator of lethality, since in all reported instances, the mean values for plasma norepinephrine and epinephrine were higher in nonsurviving rats. The purpose of their study was to quantitate the levels of peripheral sympathetic activation as indicated by plasma catecholamine levels during sepsis. The actual reason for the increase was not the primary focus and possible blockage of re-uptake at neuronal sites was not addressed.

Although bacteria lack a nervous system and, thus, have no apparent need for neurotransmitters such as norepinephrine, epinephrine and dopamine, I have recently discovered that the presence of these chemicals in their environment may positively or negatively influence the growth of Gram-negative or Gram-positive bacteria. Based upon this discovery, I have devised a method of treatment of the pathologic state of a patient in order to modulate the growth of such infectious agents, as well as regulate viral, phage, plasmid, microorganism, or parasite reproduction.

Such a class-dependent response presents great opportunity for novel approaches in drug design. For example, the identification of the receptors by which bacteria may use these neurochemicals leads to the design of receptor antagonists which may be as potent in the control of bacterial growth as current antimicrobial therapy, including the application of antibiotics. Gram-negative bacteria having a growth-enhancing response to neurochemicals are open to treatment by any inhibitor which intercedes at any point in the catecholamine biosynthetic pathway, such as monoamine oxidase inhibitors, in order to interrupt specific steps in the conversion pathways of these catecholamines.

It is accordingly a principal object of the present invention to provide a new and improved method for the treatment of sepsis, septicemia or septicoyemia.

Another object of the present invention is to provide a new and improved method for the treatment of living patients suffering the effects of a microbial, parasitic or viral infection.

It is yet another object of the present invention to provide a new and improved method for enhancing or suppressing the proliferation of microbial or viral agents or vectors in a living system.

A further object of the present invention is to provide a new and improved method for the suppression of bacterial replication within living patients.

Another object of the present invention is to provide a new method for specifically binding the novel receptor identified herein.

Yet another object of the present invention is to provide a new method for application in the field of the design of drugs and therapeutics, by which recognition of this novel receptor identified herein is useful in suppressing the proliferation of infectious agents.

SUMMARY OF THE INVENTION

The foregoing objects and advantages of the invention are achieved by providing a method of applying a neurochemical to a substrate or living patient for the purpose of modulating the growth of infectious agents such as bacteria, parasites or viruses. I have found that the addition of such neurochemicals to cultures of Gram-negative bacteria, such as *Escherichia coli* and *Yersinia enterocolitica*, can cause vast increases in bacterial growth capacity, depending upon the concentration of neurochemical and initial bacterial load in the culture. The reaction involved is very specific, since a similar response has not been evoked by any of the metabolites of norepinephrine or epinephrine, except in *E. coli*. Conversely, these catecholamines can suppress the growth of Gram-positive bacteria, such as *Staphylococcus aureus*. This class-dependent response heretofore unrecognized presents great opportunity for novel approaches in drug design.

The modulation of bacterial growth is effected in vitro by the addition of one or more catecholamines to buffered basal culture medium containing the subject bacterial cells and control or catecholamine solution in an amount ranging from about $10^{-4}$ to $10^{-10}$M concentration. Modulation of growth rate can be detected by a number of standard methodologies. For example, scintillation counts of $^3$H-thymidine, optical density readings or plate counts may be performed. In order to examine whether the ability of the catecholamines is modulated by known receptors, known antagonists which specifically block receptor binding of catecholamines, such as norepinephrine and epinephrine, may be added to bacterial cultures in the presence or absence of a preselected concentration of norepinephrine. Known agonists are also tested.

Accordingly, a method of treatment of infections has been devised in which treatment protocol is based not upon whether the causative agent is infectious, but upon the nature of the cell wall in microorganisms (or other binding characteristics in viruses or vectors). It has been discovered that growth is enhanced in Gram-negative microbes when in the presence of certain catecholamines. Thus, the accepted practice of administering catecholamines in such patients should be suspended. However, growth of Gram-positive bacteria is suppressed in these conditions, which contraindicates suspension. Because the affinity of these microorganisms for certain catecholamines is receptor-mediated, as demonstrated herein, the method of treatment of infections caused by these organisms is directed at manipulation of the receptor. Furthermore, the receptor involved is not blocked by known $\alpha_1$, $\alpha_2$ or $\beta$ adrenergic agents.

These discoveries have important industrial applications as well. Thus, a method of including one or more catecholamines in the culture medium for such organisms is described. When growth is stimulated, the production of desirable by-products is augmented. The method of stimulating this growth is directed at the specific receptor involved.

Other objects of the present invention and many of its attendant advantages will be more readily appreciated as the invention becomes better understood by reference to the following detailed description when considered in connection with the accompanying drawings in which like reference numerals designate like parts throughout.

Figure 3:
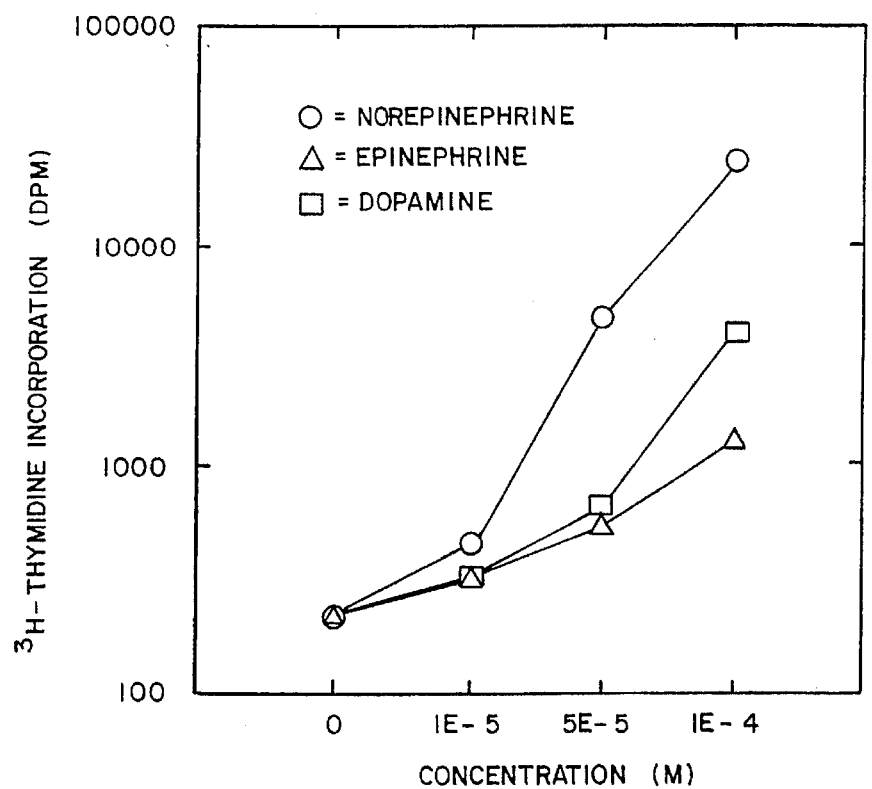
FIG. 3 is a plot illustrating differing rates of thymidine incorporation into newly synthesized DNA when *E. coli* is cultured in various concentrations of norepinephrine, epinephrine and dopamine at an initial inoculum of 15 CFU per well.
Figure 4:
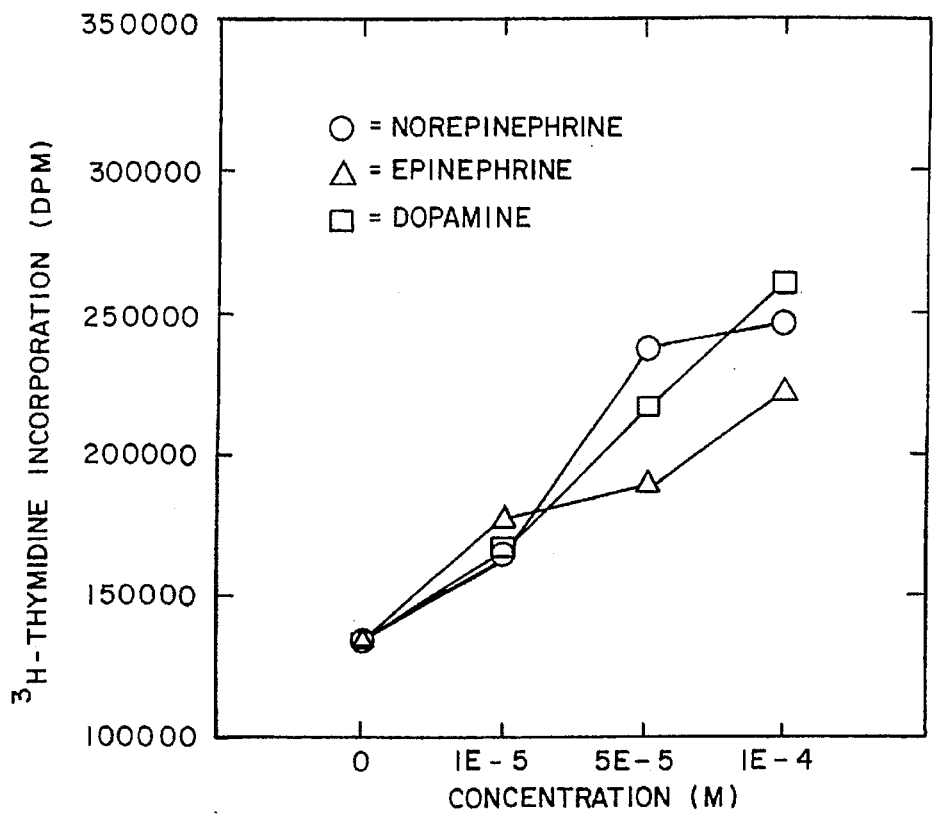
FIG. 4 is a plot similar to FIG. 3 illustrating differing rates of $^3$H-thymidine incorporation into newly synthesized DNA when *E. coli* is cultured in various concentrations of norepinephrine, epinephrine and dopamine at an initial inoculum of 1500 CFU per well.
Figure 5:
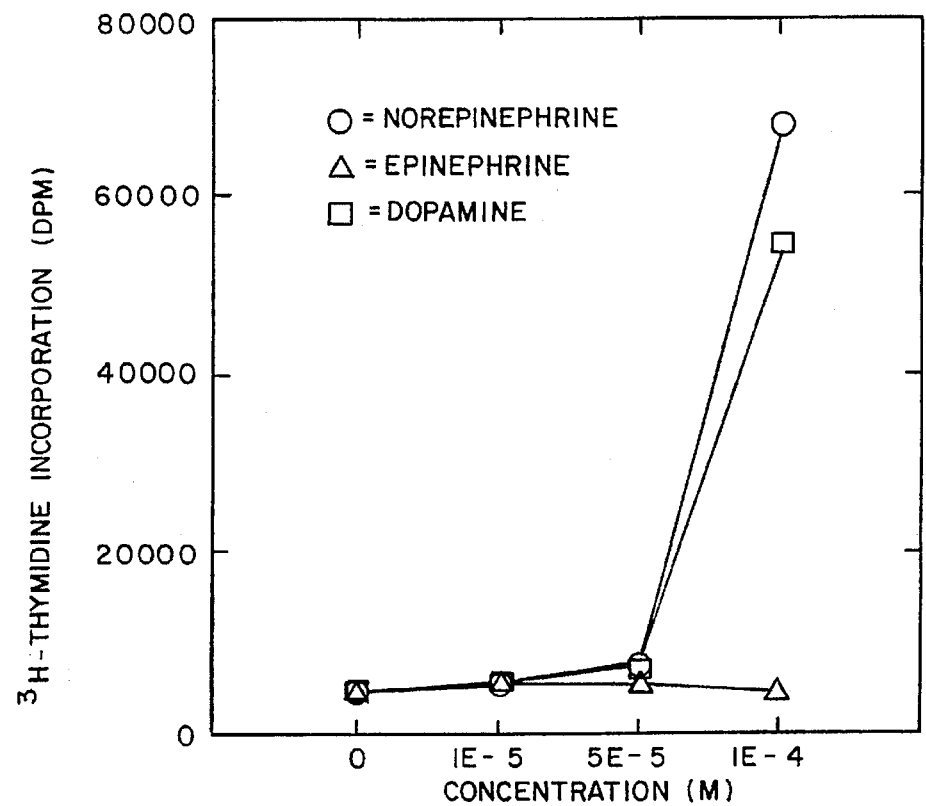
FIG. 5 is a plot illustrating the differing rates of $^3$H-thymidine incorporation into newly synthesized DNA when *Y. enterocolitica* is cultured in various concentrations of norepinephrine, epinephrine and dopamine at an initial inoculum of 10,000 CFU per well.
Figure 8:
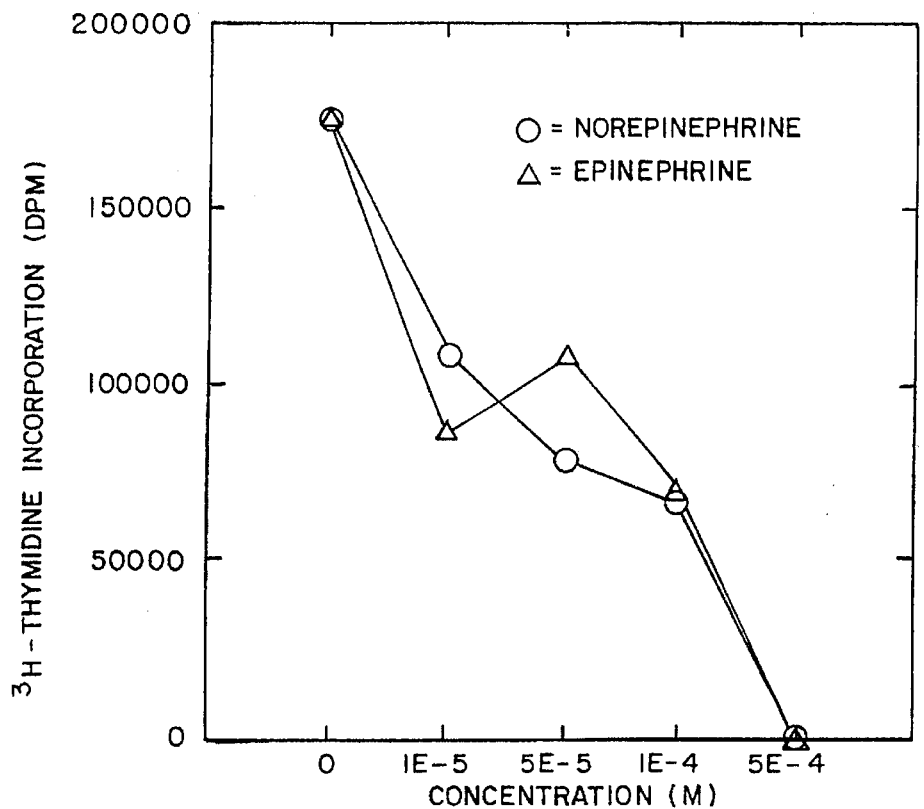
FIG. 8 is a plot illustrating differing rates of thymidine incorporation into newly synthesized DNA when *S. aureus* is cultured in various concentrations of norepinephrine, epinephrine and dopamine at an initial inoculum of 1600 CFU per well.
Figure 9:
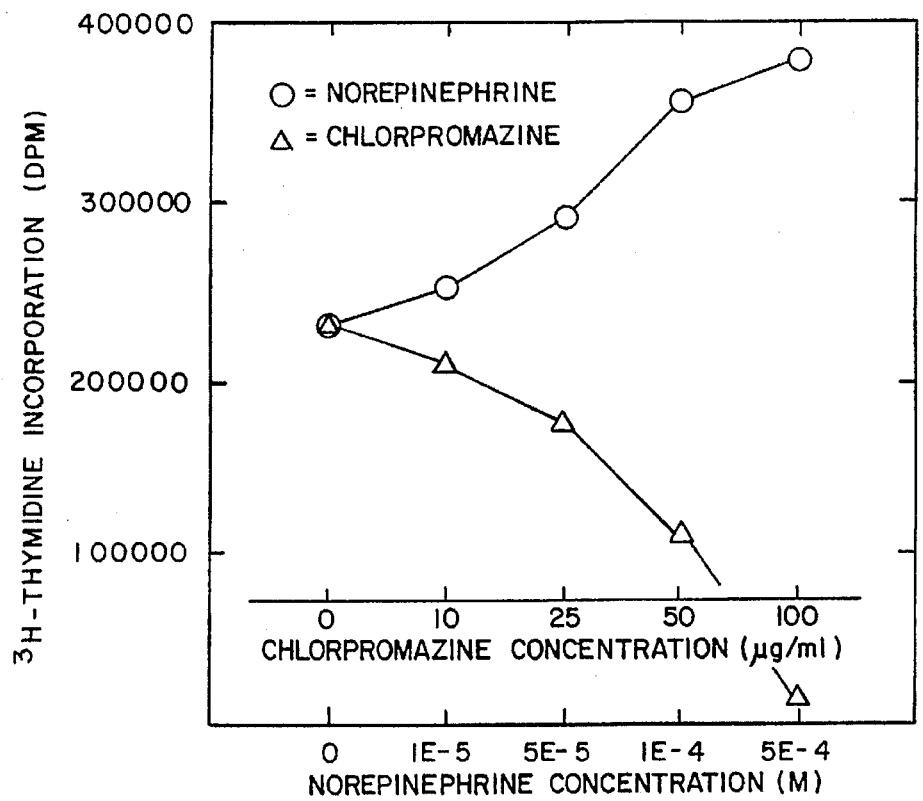
Figure 10:
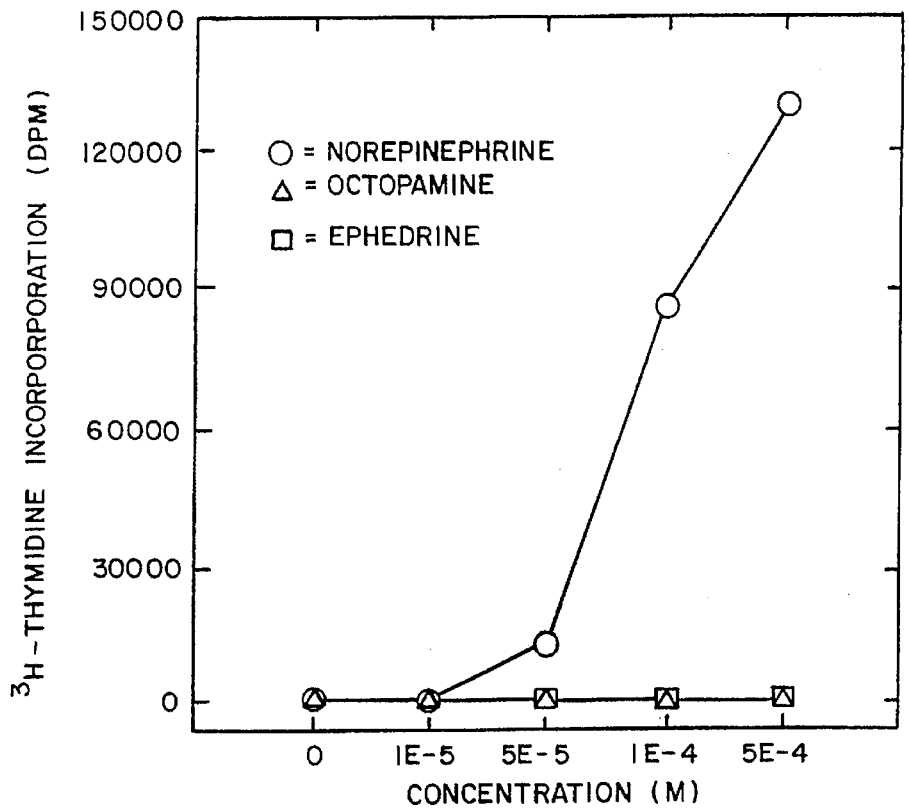
Figure 11:
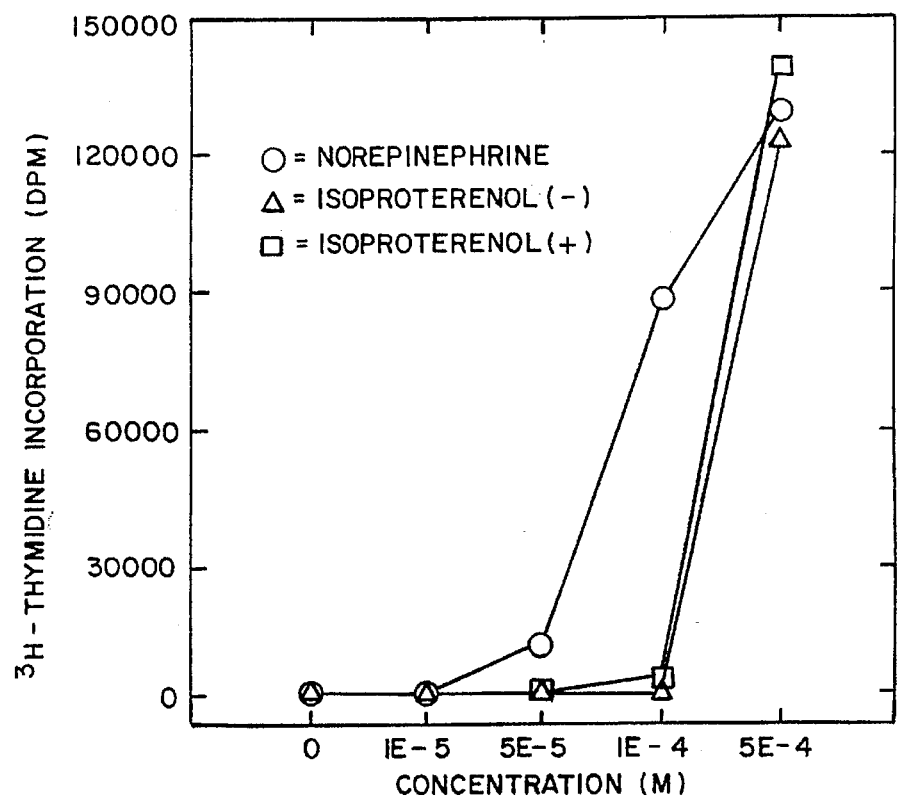
Figure 12:
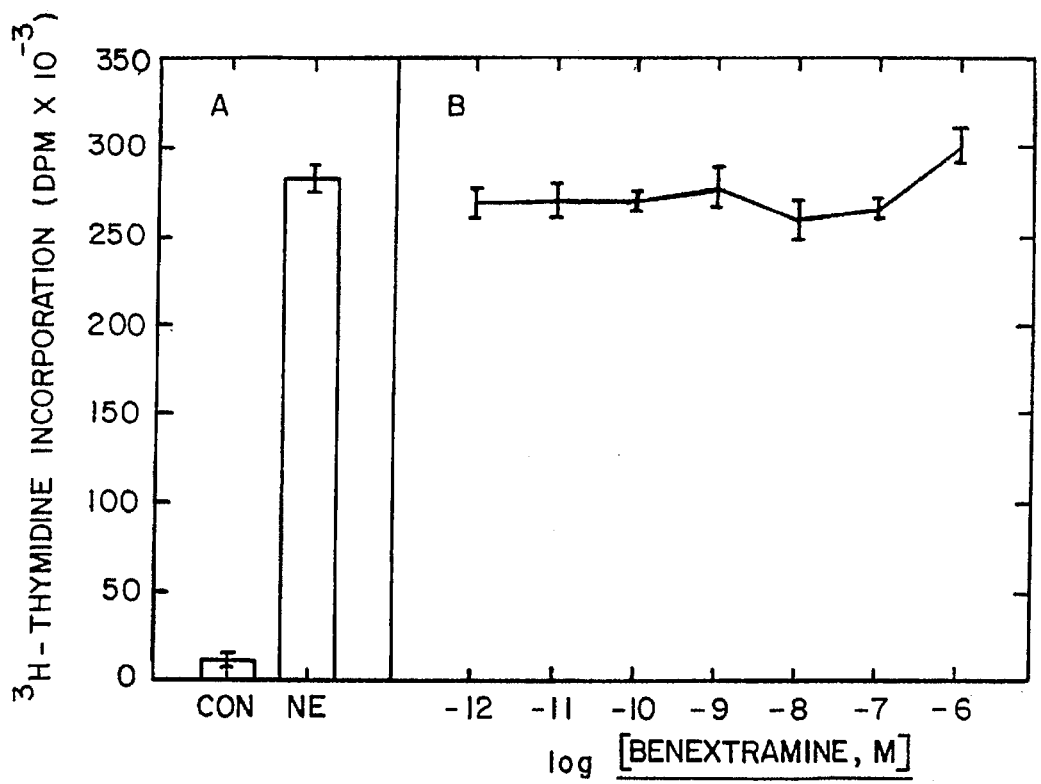
Figure 13:
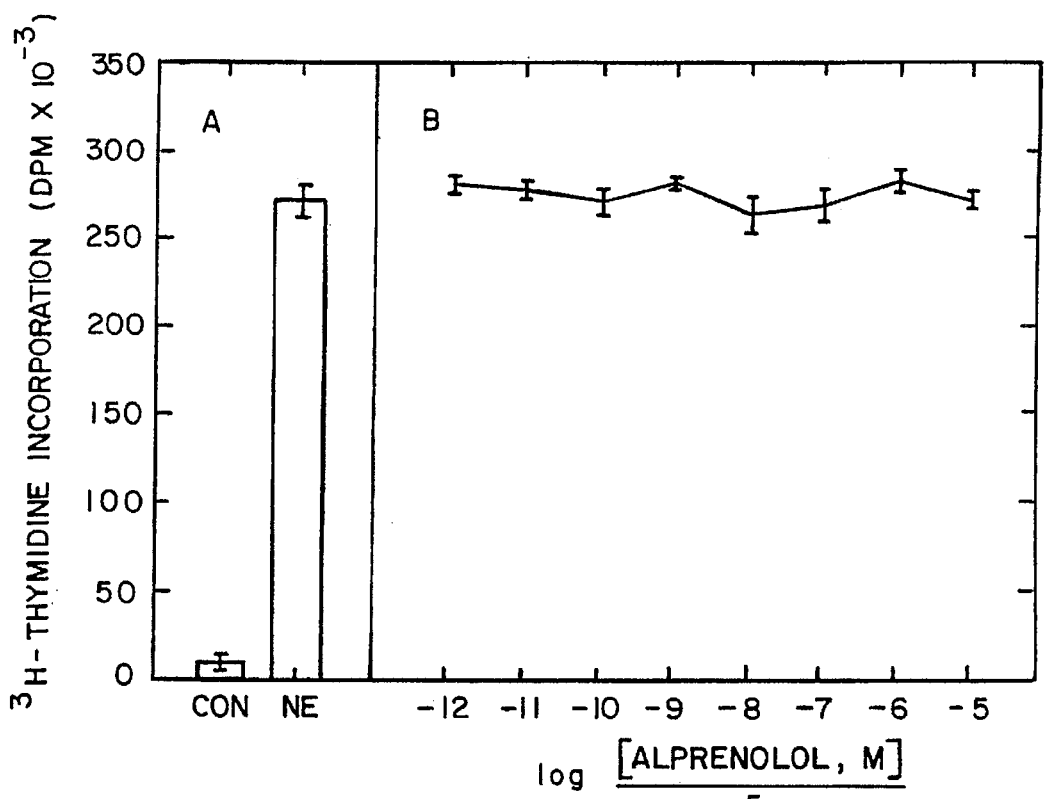
Figure 14:
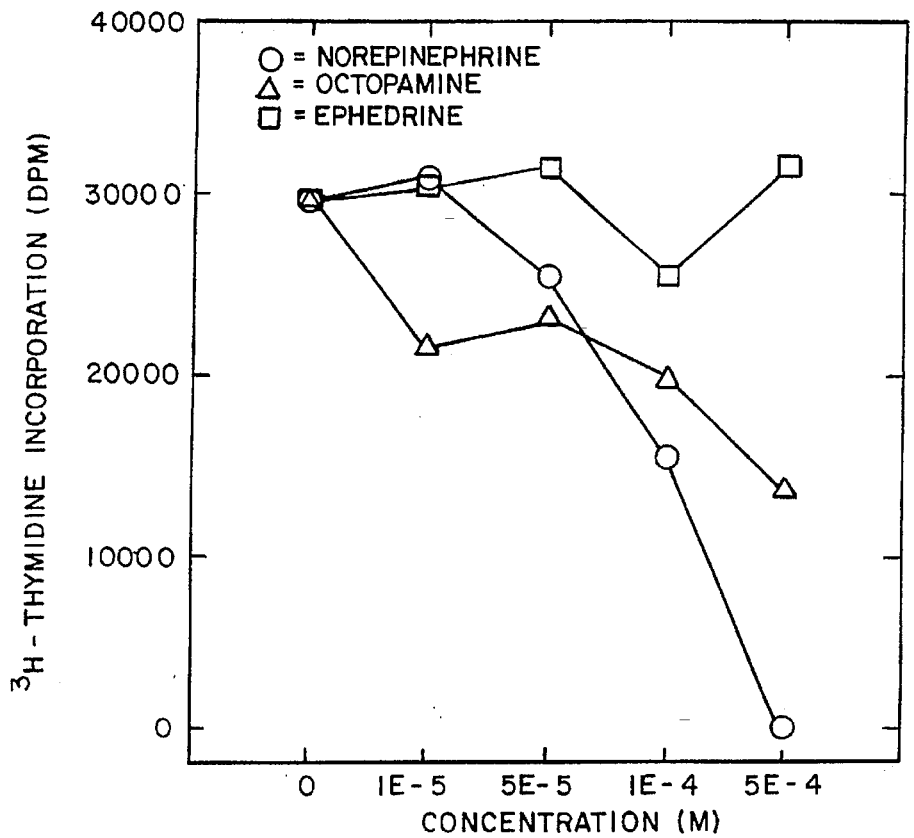
Figure 15:
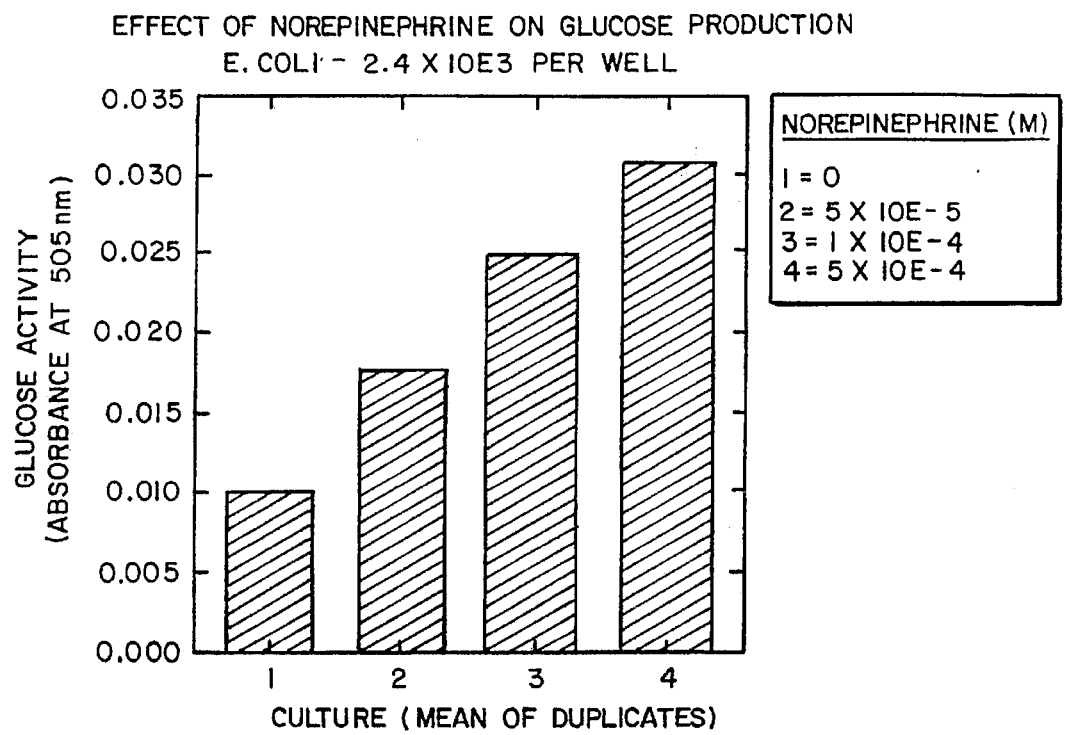
Figure 16:
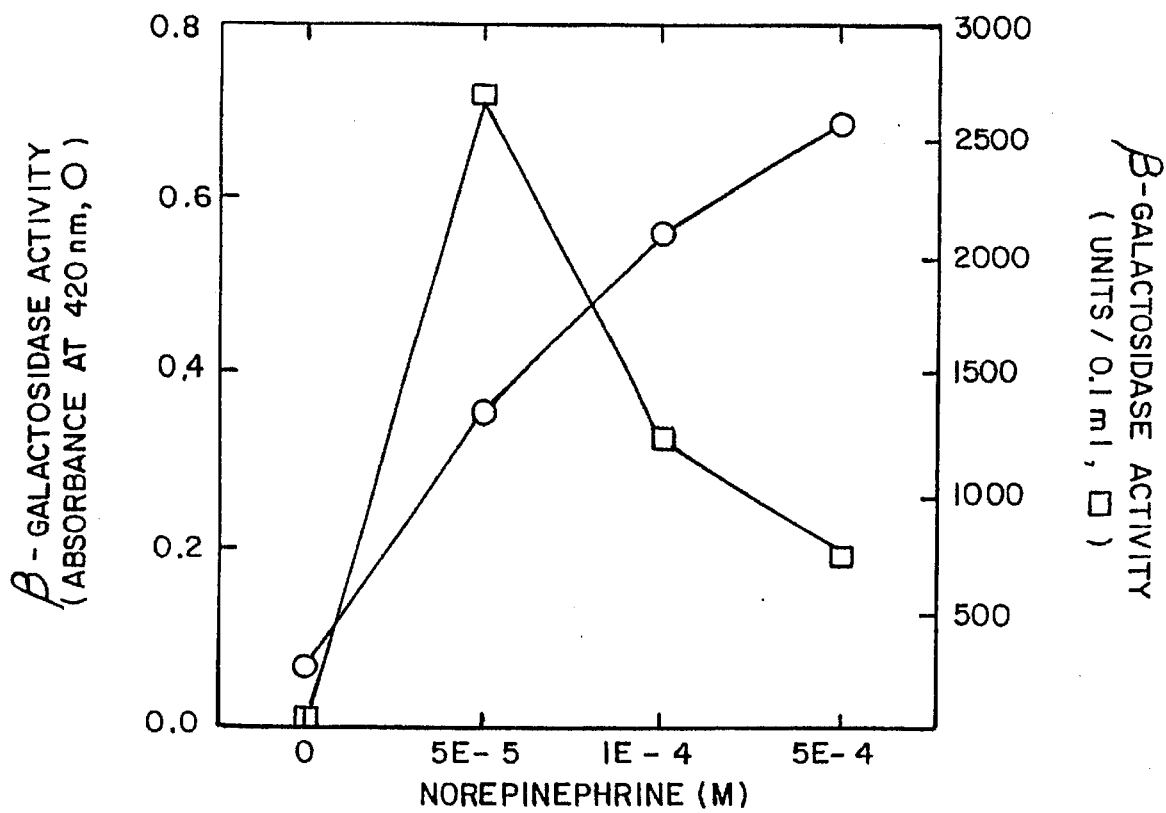
Figure 17:
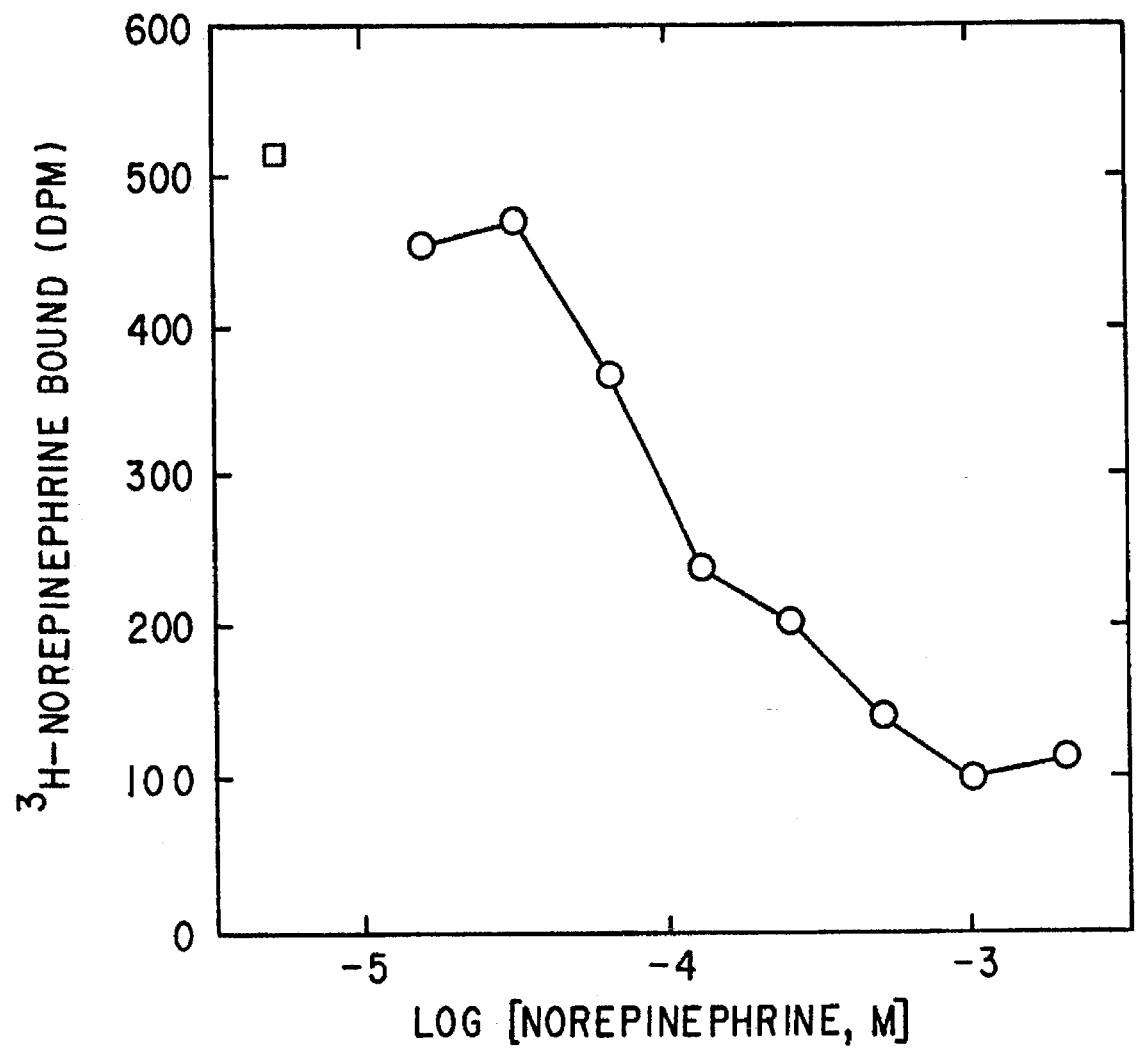
Figure 18:
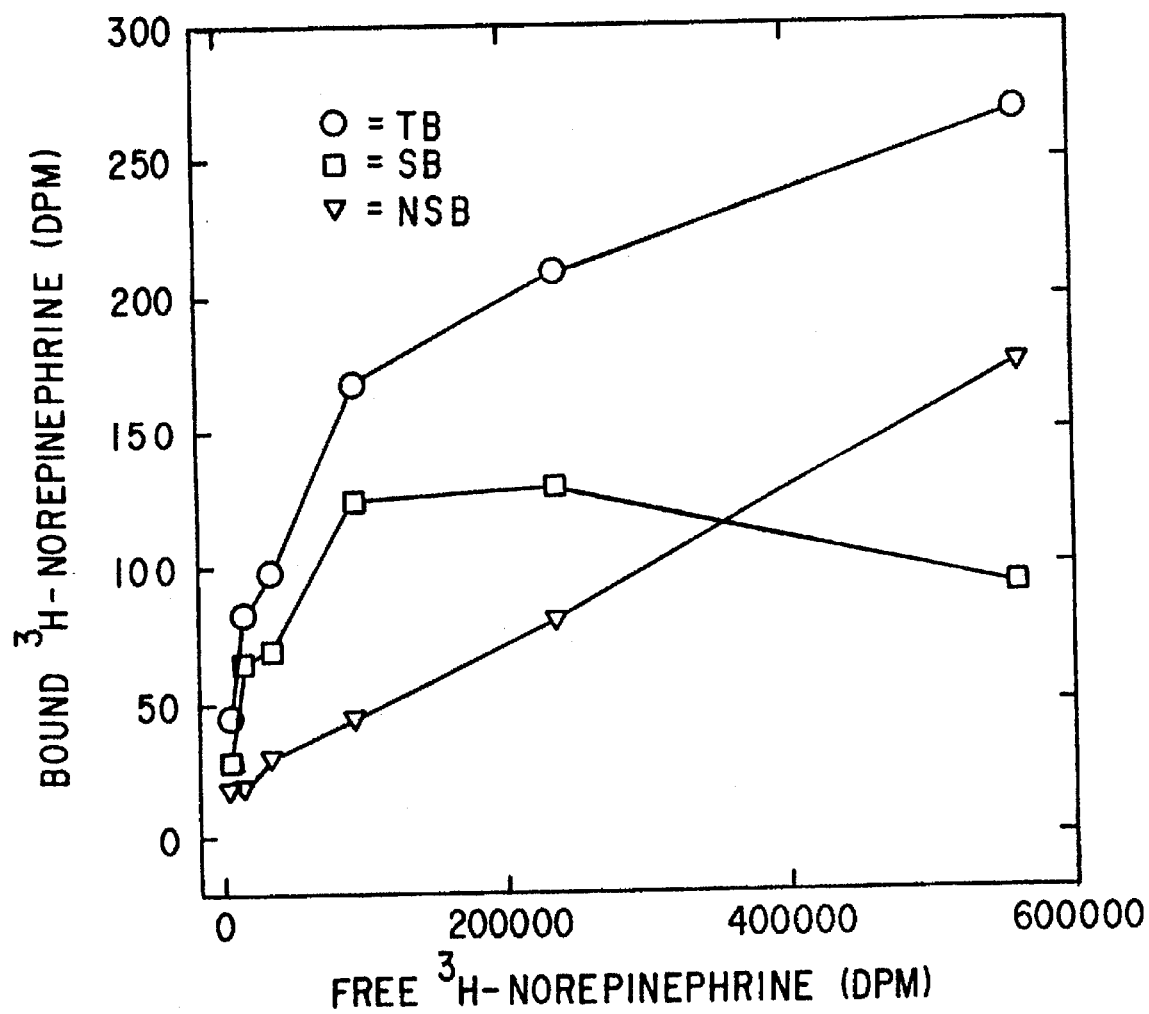
Figure 19A:
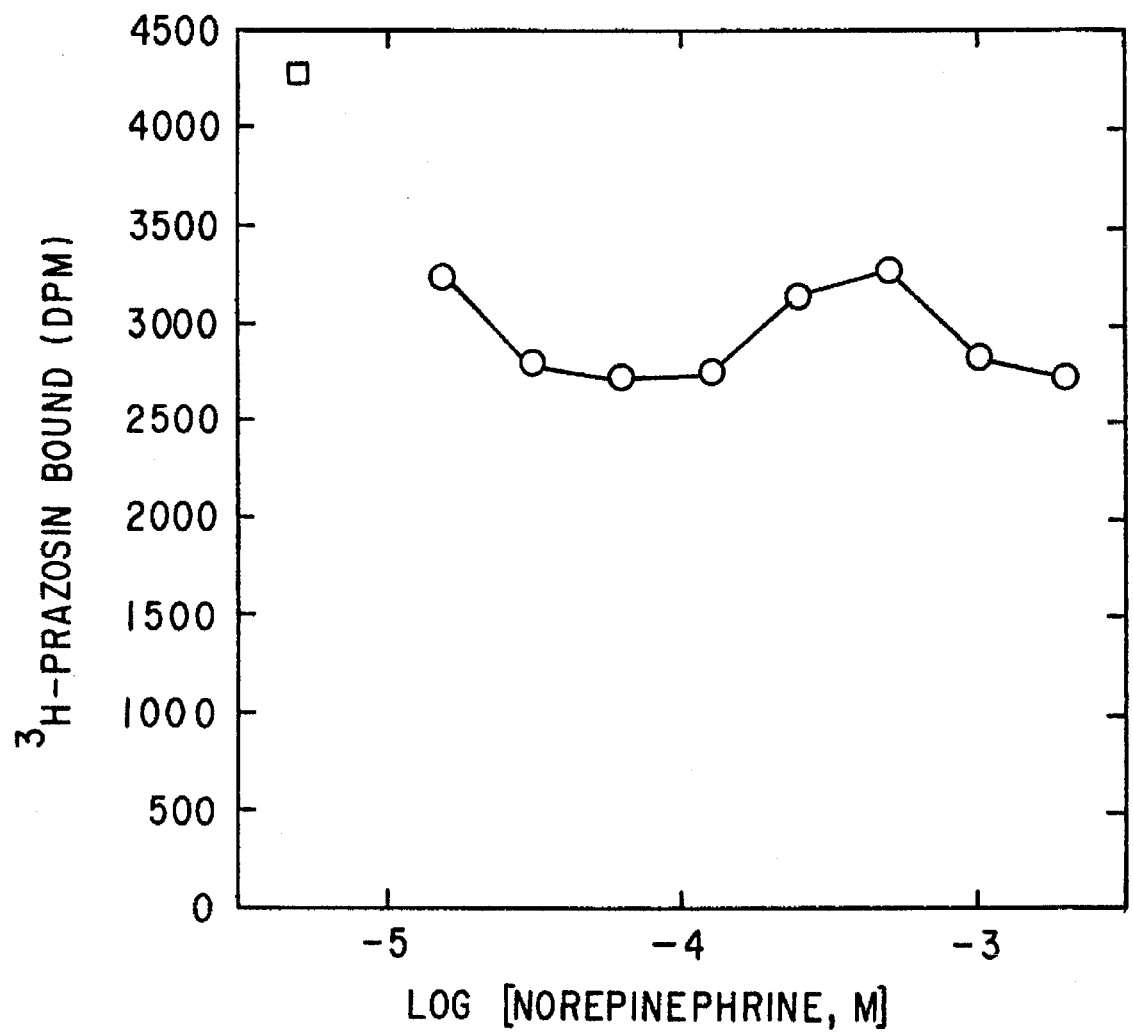
Figure 19B:
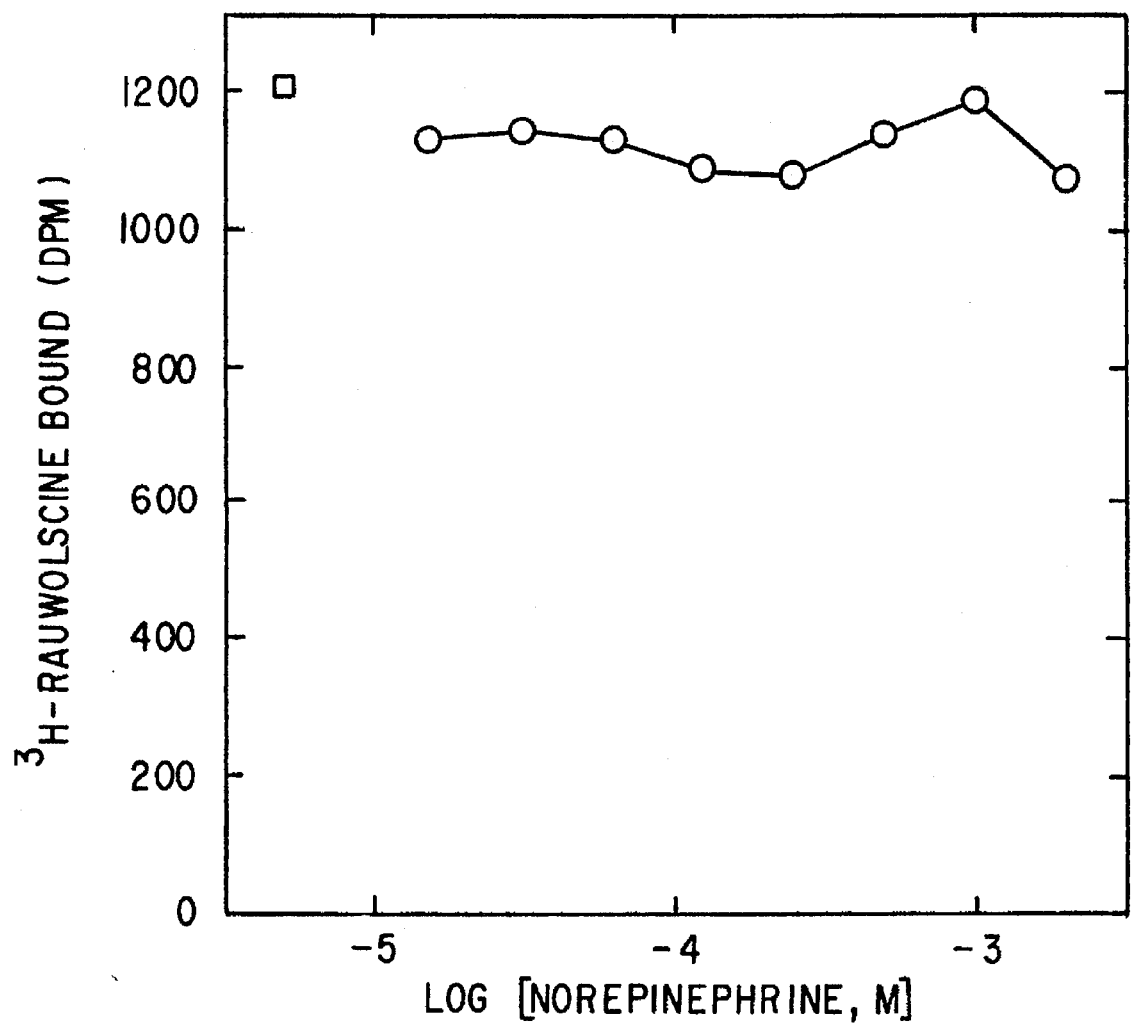
Figure 19C:
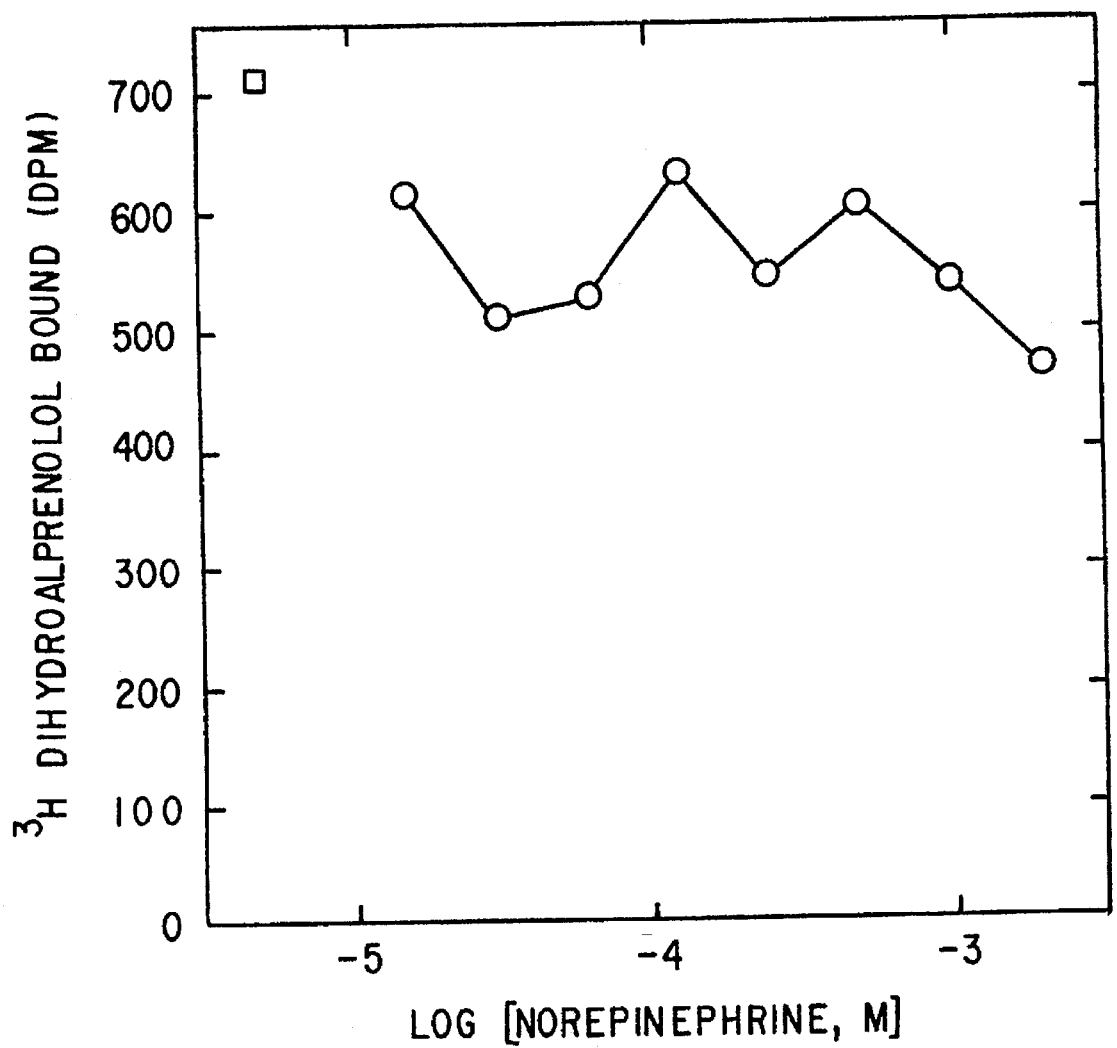
Figure 20:
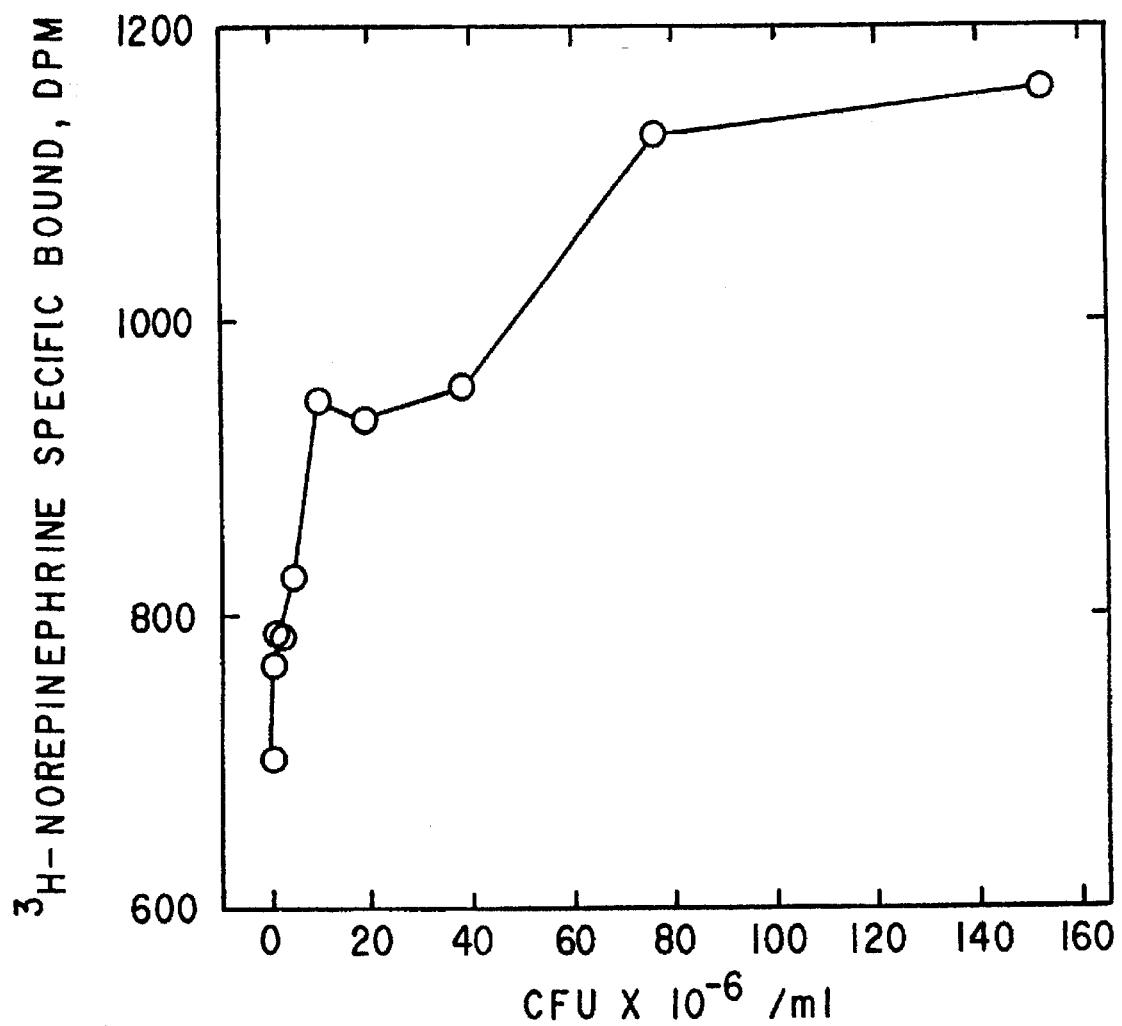

FIG. 9 is a plot similar to FIG. 8 illustrating the suppression of growth of E. coli in the presence of the antiadrenergic compound chlorpromazine with an initial inoculum of 2200 CFU per well;

FIG. 10 is a plot similar to FIGS. 8 and 9 illustrating the lack of an effect of adrenergic receptor agonists octopamine and ephedrine on the growth of E. coli with an initial inoculum of 25 CFU per well;

FIG. 11 is a plot similar to FIG. 10 illustrating the growth enhancing effect of high concentrations of the β-receptor agonist isoproterenol on the growth of E. coli at an initial inoculum of 25 CFU per well;

FIG. 12 is a plot illustrating the lack of an effect of the α-adrenergic receptor antagonist benextramine tetrachloride on growth of E. coli with an initial inoculum of 30 CFU per well;

FIG. 13 is a plot illustrating the lack of a growth enhancing effect of high concentrations of the β-adrenergic receptor antagonist alprenolol on the growth of E. coli at an initial inoculum of 25 CFU per well;

FIG. 14 is a plot similar to FIG. 10 illustrating a lack of decrease in growth of S. aureus in the presence of the dual α- and β-adrenergic receptor agonist ephedrine at an initial inoculum of 27 CFU per well;

FIG. 15 is a graph illustrating the increase in glucose production at increasing concentrations of norepinephrine in cultures of E. coli;

FIG. 16 is a plot illustrating the increase in β-galactosidase activity with increasing concentrations of norepinephrine in cultures of E. coli;

FIG. 17 is a graph illustrating a $^3$H-norepinephrine competition/displacement curve;

FIG. 18 is a saturation curve for $^3$H-norepinephrine;

FIG. 19A is a competition/displacement curve illustrating the non-displacement with non-specific binding which occurs with the addition of $^3$H-prazosin;

FIG. 19B is a competition/displacement curve illustrating the non-displacement with non-specific binding which occurs with the addition of $^3$H-rauwolscine;

FIG. 19C is a competition/displacement curve illustrating the non-displacement with non-specific binding which occurs with the addition of $^3$H-dihydroalprenolol;

FIG. 20 is a tissue dependency graph demonstrating saturation in which all of the novel receptors are saturated with catecholamines at high concentrations of bacteria;

FIG. 21 contains Table 1 which depicts data representative of the contents of FIGS. 3–5 and further includes data on the effective administration of catecholamine metabolites and is also referred to as "Table 1"; and FIG. 22 contains Table 2 which demonstrates the effective norepinephrine and various α- and β-receptor agonists on the growth of Y. enterocolitica and is also referred to as "Table 2".

DESCRIPTION OF THE PREFERRED EMBODIMENT

Sepsis, or any of the related septic injuries or conditions, evokes a multiplicity of organ system responses, some of which are directed at maintaining cardiovascular and metabolic homeostasis. Concomitant, increased peripheral sympathetic nerve activity may result in an increase in circulating catecholamines in order to stimulate peripheral adrenergic receptors to support the cardiovascular and metabolic processes which may be interrupted or impaired by sepsis. Thus, it is common to administer norepinephrine and dopamine during a period of sepsis in order to enhance and stabilize hemodynamics. Cardiovascular processes may be enhanced by augmented cardiac output, whereas other metabolic processes may be improved by, for example, increased mobilization of liver glycogen.

Observation of the typical post-hospitalization outcome of such patients indicates that following an initially successful response to antimicrobial therapy, there is a re-infection effect that eventually results in the death of up to 60% of this population. Previously, these deaths have been attributed to nonspecific causes such as generalized organ failure. It has been noted, however, that a vast majority of these deaths have followed a Gram-negative infection and that the primary causative vector was E. coli. The present invention is concerned with a method of treatment of these patients that for the first time explains this rebound effect in terms of environmental conditions previously believed to be nonsupportive of microbial growth, but which, in fact, actually augment growth, as described hereinafter.

The modulation of microbial growth may be effected in vitro by the addition of one or more catecholamines in an amount ranging from about $10^{-4}$ to $10^{-10}$M concentration to culture medium containing the subject microbial cells. Depicted at Block 1 of FIG. 1, the culture medium should preferably be a relatively simple medium so as to facilitate the inclusion of the catecholamines in a known concentration. For example, a basal medium consisting of various constituents such as dextrose (0.5 g/l, 2.78 mM), ammonium nitrate (0.5 g/l, 6.25 mM), potassium phosphate (0.25 g/l, 1.84 mM), potassium chloride (0.25 g/l, 3.35 mM) and magnesium sulfate (0.25 g/l, 1.01 mM) adjusted to a final pH of 7.5. Additionally, hepes buffer may be added at a final concentration of 10 mM to provide additional buffering capacity. This medium may then be further supplemented with 30% V/V of bovine serum, although equivalent results may be obtained with serum from other sources such as pig, mouse and man. Suitable antioxidants such as ascorbic acid may also be added to prevent oxidation of catecholamines. However, such compounds should be used judiciously, since the antibacterial effects of antioxidants are well recognized. It is recognized that individual cells may require different basal medium preparations to insure optimum growth in catecholamine supplemented medium.

Figure 1:
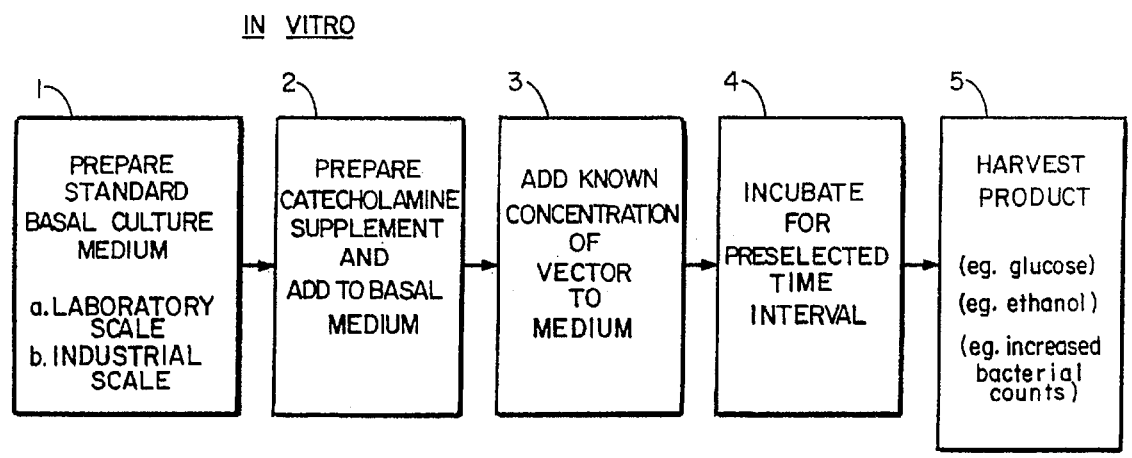
FIG. 1 is a block diagram of a preferred embodiment of the method of the present invention for in vitro applications.

As depicted at Block 2 of FIG. 1, the desired catecholamine is then dissolved in an appropriate amount of chilled boiled water. The catecholamine solution is then added to the basal medium in a final volume-to-volume addition of, for example, 20%. The subject microbial cells are prepared in serum supplemented basal medium at varying concentrations of 15 to 15,000 CFU per ml and as depicted at Block 3, 100 µl of suspensions may be added into the wells of standard tissue culture plates. Next, 100 µl of catecholamine or control solution is added to the wells containing, for example, bacteria and the plates are incubated for varying lengths of time at an appropriate temperature in a humidified incubator, as at Block 4. This process may be altered as necessary for application to a variety of non-microbial vectors as well.

Modulation of growth rate can be detected by a number of standard methodologies. For example, the cultures can be further supplemented at time of culture initiation by the addition of 50 µl of a 20 µCi solution of $^3$H-thymidine in PBS per 200 µl of culture. Culture contents can then be harvested onto filter mats using standard plate harvesters which separate unbound radioactive material from radioactive material that has been incorporated into the cell's DNA. The filter mats with bound material are then counted in a scintillation counter. The raw counts resulting from incorporation of the $^3$H-thymidine into newly synthesized DNA is used as measure of cell proliferation. The greater the counts, as compared to cells incubated in the absence of catecholamines, the larger the enhancement of proliferation, and vice versa. Alternatively, contents of plate wells may be gently resuspended and the optical density readings taken in a standard microplate reader at an optical density of 550 nm or 630 nm. Increases in optical density readings in catecholamine supplemented wells as compared to control wells indicates greater mass of cells due to increased proliferation. Further, plate counts may also be performed by standard pour-plate methodology in which the contents of the plate well are gently resuspended and an aliquot removed and serially diluted samples are plated. After 24–48 hours, the number of colonies are enumerated with an increase in colonies relative to control plates indicating enhanced cell proliferation.

As depicted at Block 5, certain by-products may arise as a consequence of the growth of microbes in appropriately selected media. For example, the growth of *E. coli* in a lactose broth will yield glucose. In the stimulating presence of catecholamines, as documented more fully hereinafter, this yield is increased due to an increase in proliferation. Thus, increases in such yield have great commercial potential. In appropriate circumstances, the microbes themselves may be harvested, or their products may be used as intermediates for other products. An example of the later is the use of microorganisms containing a genome for the conversion of glucose to ethanol.

Figure 2:
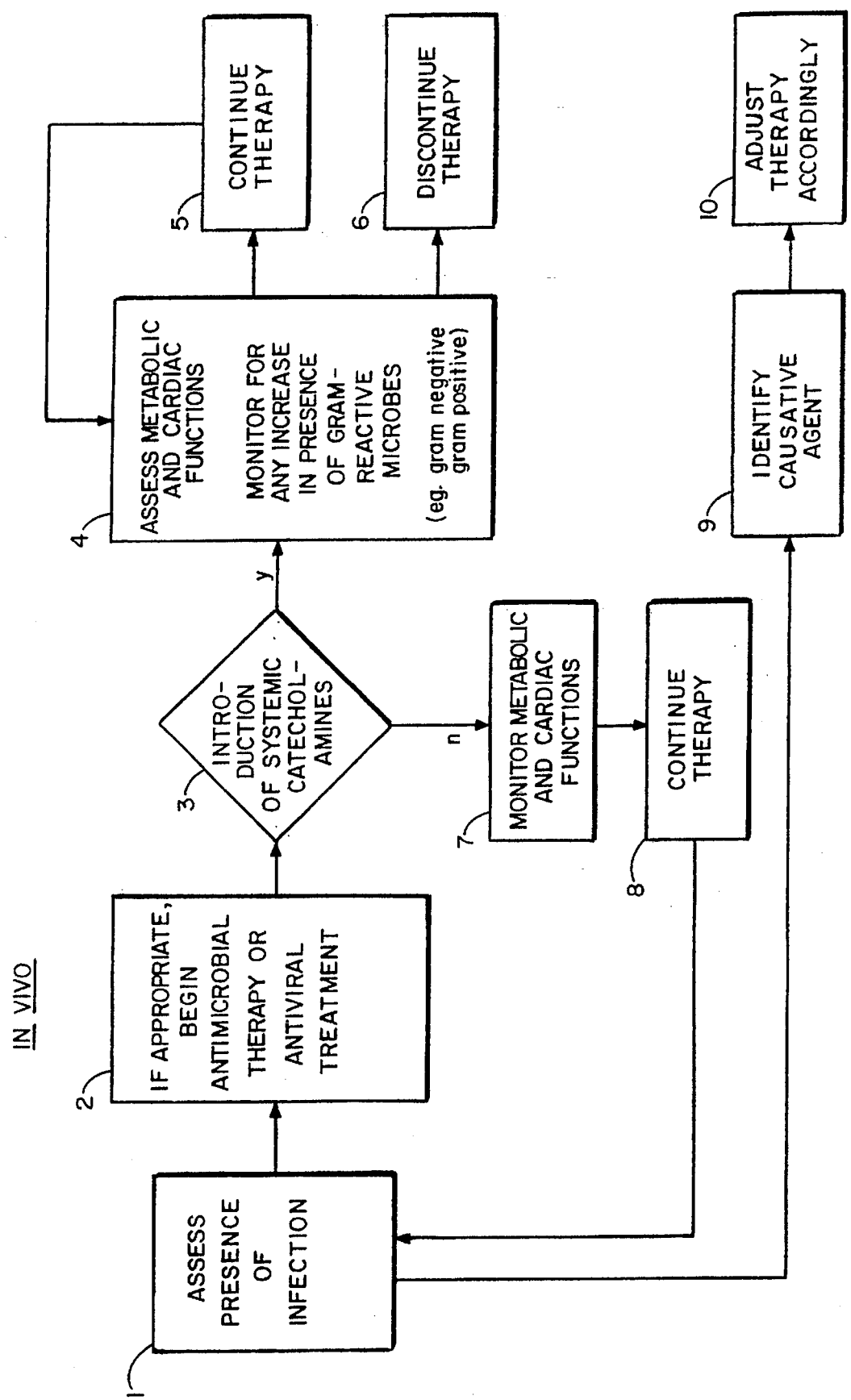
FIG. 2 is a block diagram of an alternative embodiment of the present invention for in vivo applications.

FIG. 2 depicts a method for in vivo treatment of infection using a suggested method of the present invention. As denoted at Block 1, the causative nature of the infection must first be assessed. Once the microbe, virus or vector has been identified, the appropriate therapy is commenced, as at Block 2. This therapy would include either application of antimicrobial or antiparasitic agents, or pertinent anti-viral treatment. Depending upon the nature of the causative organism and resultant effects or hemodynamics, a decision must be made as to whether or not to introduce systemic catecholamines to the patient, as designated at Block 3. If the decision is reached that catecholamines should be applied, metabolic and cardiac functions should be monitored as denoted at Block 4. As described further hereinafter, it is also appropriate at this time to screen for any increase in the concentration of microbes, whether Gram-negative or Gram-positive. The therapy commenced at Block 2 should be continued (Block 5) with intermittent assessment and monitoring, as denoted at Block 4. Otherwise, therapy should be discontinued (Block 6). If, however, the decision is made that due to the nature of the causative organism, catecholamines should not be applied, subsequent steps denoted at Blocks 7 and 8 include monitoring of metabolic and cardiac functions as well as a continuation of appropriate anti-microbial or anti-viral therapy.

Concomitant to the steps described in Blocks 1 through 8, appropriate steps are taken at Block 9 to identify the agent causing the infection. It is to be emphasized that these steps (Block 1 and Block 9) are undertaken simultaneously, due to the customary time delay in arriving at a proper identification and the deleterious impact which would ensue if therapy were delayed. Once the agent is identified, it may be necessary to alter or adjust therapy accordingly, as at Block 10.

The incorporation of circulating catecholamines, specifically norepinephrine and epinephrine, into mammalian neuronal fibers during re-uptake is accomplished via receptors. These include the $\alpha$- and $\beta$-receptors and their constituent subtypes. In order to examine whether the ability of the catecholamines is modulated by known receptors, known antagonists which specifically block receptor binding of catecholamines, i.e., norepinephrine and epinephrine, are added to bacterial cultures in the presence or absence of a preselected concentration of norepinephrine. For example, the $\beta$-adrenergic receptor antagonist alprenolol hydrochloride (HCl) was dissolved in chilled boiled water in an amount ranging from $5 \times 10^{-4}$ to $5 \times 10^{-12}$M. Norepinephrine was also dissolved in chilled boiled water in an amount of $5 \times 10^{-5}$M. To serum supplemented basal medium, alprenolol HCl and norepinephrine were added alone or in combination. The subject bacterial cells were prepared in serum supplemented basal medium at varying concentrations of 15 to 15,000 CFU per ml and 100 µl of suspensions were added into 96 well tissue culture plates. Next, 100 µl of the alprenolol HCl alone, norepinephrine alone, or combination of varying amounts of alprenolol HCl with a constant amount of norepinephrine was added to wells containing bacteria. Additionally, 50 µl of a 20 µCi $^3$H-thymidine per ml of phosphate buffered saline was added to all wells. At preselected time intervals, optical density readings were taken and immediately thereafter, wells were harvested using a standard plate harvester. The amount of radioactive incorporation of the $^3$H-thymidine was determined using a scintillation counter. The ability of the antagonist alprenolol HCl to block the norepinephrine induced enhancement of proliferation through blockage of the known $\beta$-adrenergic receptor would be reflected in a reduction in counts as compared to cultures supplemented with norepinephrine alone.

All data points in the following Figures represent mean quadruplicate cultures and all points have a standard error of the mean of less than or equal to 10%. Experimental methods include standard radioligand techniques to assess the incorporation of $^3$H-thymidine into newly synthesized DNA. Control values are designated CON. Commercially available norepinephrine and epinephrine were obtained in the hydrochloride and bitartrate forms. Efficacy was not found to be form-dependent. The hydrochloride form of dopamine was used.

FIG. 3 depicts a positive correlation between increase in concentration of a Gram-negative bacterium and increased $^3$H-thymidine incorporation (DPM) into newly synthesized DNA in the presence of the catecholamines norepinephrine, epinephrine and dopamine. Data presented are for a 10-hour culture of *E. coli* with an initial inoculum of 15 colony-forming units (CFU) per well. Of these catecholamines, it can be seen that norepinephrine is the most potent enhancer of growth at low initial concentration of Gram-negative bacterium.

To show that the effect depicted in FIG. 3 was not dependent upon the initial concentration of bacterium, experiments were repeated at a variety of initial concentrations. For the Gram-negative bacterium, *E. coli*, all concentrations revealed the same growth enhancing trend. Accordingly, FIG. 4 depicts a 10-hour culture of *E. coli* with an initial inoculum of 1500 CFU per well. When normalized for initial concentration, it becomes apparent that the percent increase in $^3$H-thymidine incorporation (DPM) for each catecholamine is less than the percent increase depicted in FIG. 3 for a lower initial concentration. This is explained on the basis of normal growth dynamics in which the stationary phase is approached in a shorter time when there is a heavy initial inoculum than when the initial inoculum is very light. Accordingly, any effect caused by a growth enhancing factor will appear greater in a light inoculum than in a heavy one.

A variety of Gram-negative organisms were tested under these conditions, and it was discovered that the growth enhancing effect of norepinephrine was consistent and not species-specific. For example, FIG. 5 depicts a 36 hour culture of *Yersinia enterocolitica* with an initial inoculum of 10,000 CFU per well. The data represented herein were selected because they presented typical values for incorporation of $^3$H-thymidine into newly synthesized DNA at high concentration of catecholamine. The enhancing effect of catecholamines is representative of all tested Gram-negative bacteria at high initial concentrations. No Gram-negative organism was found which did not demonstrate a selective preference for one or more of the catecholamines tested.

Table 1 depicts data representative of the contents of FIGS. 3 through 5 and further includes data on the effect of administration of catecholamine metabolites. These data confirm the impression presented in FIGS. 3 through 5 that *Y. enterocolitica* is considerably more selective in substrate usage than *E. coli*. The ubiquitous nature of *E. coli* is borne out by the fact that it is even capable of fueling growth by utilization of the metabolites 4-hydroxy-3-methoxyphenylglycol piperazine salt (MHPG) and normetanephrine (NOR). Data represent mean DPM values with initial concentrations of 15 and 1500 CFU for *E. coli* and 80 CFU for *Y. enterocolitica*. The mean DPM values were obtained from quadruplicate cultures and the standard error was 10% or lower.

Figure 6:
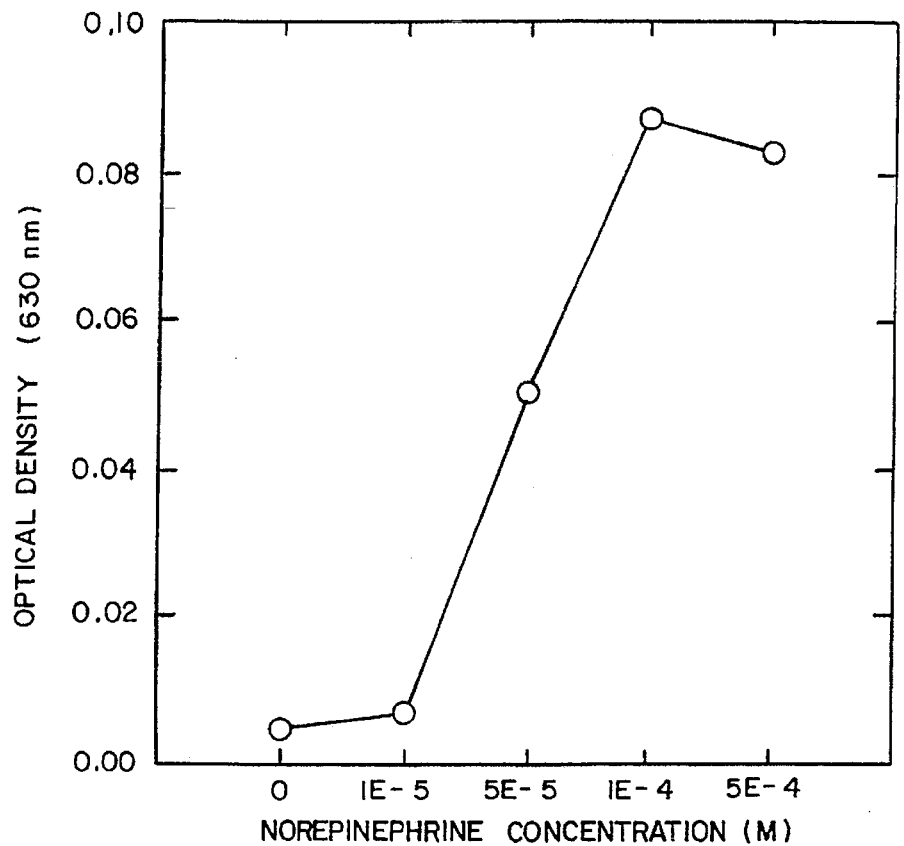
FIG. 6 is a graph illustrating the change in optical density with various concentrations of norepinephrine in a culture of *E. coli* with an initial inoculum of 25 CFU per well.

The growth-enhancing effect of norepinephrine on Gram-negative bacteria is not a method-dependent artifact. FIG. 6 depicts spectrometric data for a 20 hour culture of *E. coli* with an initial inoculum of 25 CFU per well measured at 630 nanometers. A separate blanking plate containing all media and chemicals, but lacking a bacterial inoculum, was measured to provide a correction factor for all concentrations of norepinephrine and control. The same enhancement of growth of *E. coli* was detected with this method as was shown using scintillgraphic data.

Figure 7:
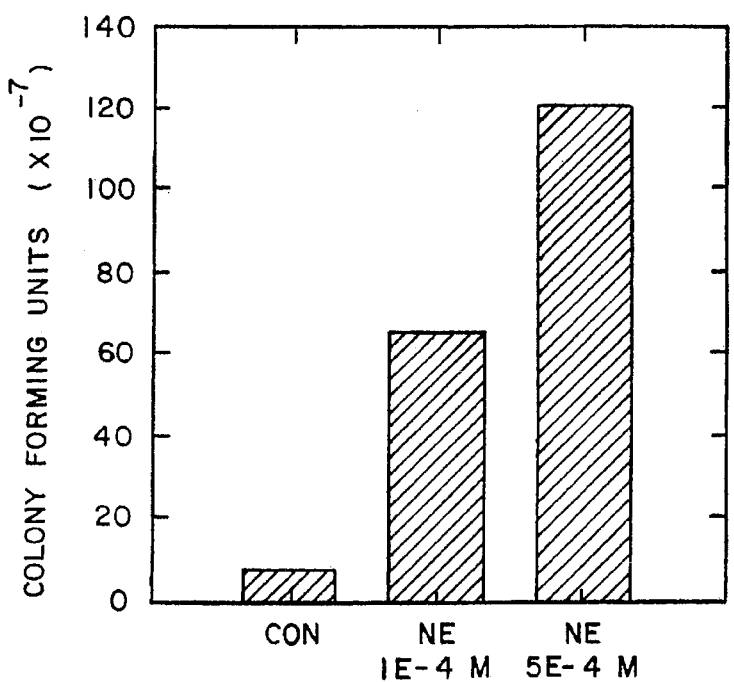
FIG. 7 is a graph illustrating pour plate counts for cultures of *P. aeruginosa* cultured in various concentrations of norepinephrine.

FIG. 7 further illustrates that the growth-enhancing capacity of norepinephrine in Gram-negative bacteria is not method dependent. In standard plate counts for a 20 hour culture of *Pseudomonas aeruginosa*, increasing concentrations of norepinephrine correlated to an increased number of mean CFU for increasing concentrations of norepinephrine as compared to a control medium lacking norepinephrine.

In dramatic contrast to the growth enhancing effect of catecholamines on Gram-negative bacteria, FIG. 8 demonstrates that these compounds have essentially the reverse effect in Gram-positive bacteria. This trend was consistent for all Gram-positive bacteria tested and exemplified by the plot in FIG. 8. A 20 hour culture of *Staphyloccus aureus* representing an initial inoculum of 1600 CFU per well manifested a decline in $^3$H-thymidine uptake into new DNA. As concentration of catecholamines increased, suppression of growth increased.

In summary, it was noted that all Gram-negative organisms tested in these studies responded positively to the introduction of norepinephrine to their growth media. Enhancement of proliferation varied between organisms, with proliferation being the most pronounced for *E. coli*. This organism was sensitive to all catecholamines tested, in contrast to the majority of Gram-negative bacteria, which were sensitive only to the presence of norepinephrine and to a lesser effect, dopamine. This effect was not method specific and was manifested at a slower rate as initial bacterial inoculum increased. In contrast, all Gram-positive bacteria tested showed a suppression of growth in the presence of the catecholamines tested. This effect was not dependent upon the initial inoculum concentration, nor on the duration of culture. Data were selected for presentation which demonstrate that the growth-enhancing effects were consistent throughout a range of conditions, and not limited to a narrow optimal range, although it is evident that certain bacteria have a selective preference for growth in the presence of one or more of the catecholamines normally available during septic crises. Furthermore, my preliminary data indicates that enhancement is not limited to bacteria and may be expected in viruses and other vectors as well.

In light of these findings, it was important to determine the effect of anti-adrenergic compounds on the growth of both Gram-negative and Gram-positive bacteria under similar conditions.

RECEPTOR

The underlying mechanism of this growth enhancement or suppression is important for the design of drugs to control sepsis. It is also important in regulation of the operons which control carbon utilization. The change in pathogenicity documented in FIGS. 3 through 8 involves receptor-mediated recognition of these catecholamines and leads to opportunity for the design of novel drugs to control growth, as described more fully hereinafter.

FIG. 9 depicts the effect of the anti-adrenergic compound chlorpromazine on the synthesis of new DNA in *E. coli*. Data presented represent an initial inoculum of 2200 CFU per well and a culture period of 11 hours. The growth suppressive effect on *E. coli* is what would be expected if the phenomena demonstrated herein were due to a receptor-mediated mechanism.

FIG. 10 delineates the lack of an effect of selected adrenergic receptor agonists upon this process. In this particular graph, the α-receptor agonist octopamine, and the dual α- and β-receptor agonist ephedrine were found to have no effect on Gram-negative growth. This particular graph presents a 10 hour culture of *E. coli* having an initial inoculum of 25 CFU per well. These findings are significant, since a growth promoting effect similar to norepinephrine would be anticipated if the underlying mechanism of this effect was any of the known α- or β-receptors.

FIG. 11 depicts the effect of active and inactive enantiomers of the β-receptor agonist isoproterenol. Although the exact mechanism of this effect has not yet been elucidated, it appears that the modality of the effect of catecholamines in these microorganisms is receptor-modulated. Thus, it would be anticipated that isoproterenol would have an effect similar to the data of FIG. 10, i.e. no effect. Conversely, at very high concentration there is, in fact, an extremely significant effect. For this reason, both the active (−) and the inactive (+) enantiomers were tested. The data presented are for a 10-hour culture of *E. coli* with an initial inoculum of 25 CFU per well. The fact that both enantiomers produced such a strong effect at high concentration leads to the conclusion that this occurrence is neither receptor specific, nor involves the commonly known β-receptors. Although all aspects have not been fully elucidated as of yet, it is presently believed that a previously unknown third type of receptor is responsible for the catecholamine-induced DNA synthesis observed. These data indicate that some type of positive interaction with this heretofore unknown receptor is being induced by such a high concentration of agonist. Similar results are also obtained with antagonists, and both sets of data appear to fall within the well-recognized non-specific effects on receptors at very high concentrations. Although not included in figure form herein, a similar effect was not obtained for other Gram-negative bacteria. For example, an essentially flat curve was obtained when these studies were repeated with *Y. enterocolitica*.

Consideration of the data presented to this point confirms what is already well known in the fields of clinical microbiology and public health, that *E. coli* holds a vast capacity for adaptation in nature. It is ubiquitous and in an infectious state, possession of a neurotransmitter receptor would greatly enhance its capacity to utilize the bodily mechanism of releasing catecholamines into the blood stream during stress to its own advantage. The data in FIG. 11 is significant in that it illustrates an ability to also utilize related compounds when such compounds are available at high concentration levels.

FIG. 12 demonstrates the lack of effect of the α-adrenergic receptor antagonist benextramine on the growth of a 20 hour culture of *E. coli* with an initial inoculum of 30 CFU per well. Referring to the bar graph designated "A", the effect of norepinephrine on *E. coli* growth is compared to control medium (CON). As illustrated in the graph labeled B, norepinephrine enhanced growth continues as anticipated irregardless of benextramine concentration. Note that the final concentration of norepinephrine is the same ($5\times10^{-5}$M).

FIG. 13 depicts the effect of the β-adrenergic receptor antagonist alprenolol on a 20 hour culture of *E. coli* with an initial inoculum of 30 CFU per well. Again, norepinephrine stimulates growth in comparison to control and the presence of alprenolol has no inhibiting effect on norepinephrine enhanced growth, as depicted in graph "B". Graph A demonstrates norepinephrine-induced growth in the absence of alprenolol.

FIG. 14 demonstrates the effect of a dual α- and β-receptor agonist, ephedrine, on a 20 hour culture of *Staphyloccus aureus* with an initial inoculum of 27 CFU per well. The growth of this Gram-positive bacterium is not decreased in the presence of this agonist as it is in the presence of norepinephrine. In light of these results, the α-receptor agonist, octopamine, was tested and found to produce some inhibition of growth. This is somewhat analogous to the events in FIG. 11 involving active and inactive enantiomers of isoproterenol.

Table 2 demonstrates the effect of norepinephrine and various α- and β-receptor agonists on the growth of *Y. enterocolitica*. Mean DPM values were obtained for quadruplicate cultures of the indicated compounds. The standard error of the mean did not exceed 10%. Concentrations for all compounds are $10^{-4}$M. Abbreviations are: 0, control (no compound added); NE, (−)-norepinephrine; OCT, (−)-octopamine; (−)-isoproterenol; (+)-isoproterenol; and (−)-ephedrine. Values shown were obtained at 36 hours. The number of colony forming units for CON indicates the number of bacteria present in each well at initiation of culture. Once again, the significant growth enhancing effect of norepinephrine is evident in view of insignificant effect by related α- and β-agonists.

To summarize the contents of FIGS. 9–14, receptor blockade by known α- and/or β-antagonists neither induced nor inhibited the growth of Gram-negative bacteria. Similarly, the introduction of α- or β-agonists in moderate quantities to cultures of Gram-positive organisms or in small to large quantities to cultures of Gram-negative organisms had no effect upon growth. A slight decrease in growth was detected when the Gram-positive bacterium *S. aureus* was grown in the presence of large quantities of the α-agonist, octopamine. These data indicate that a receptor-mediated process is involved, but it does not utilize the known α- or β-adrenergic receptors. Although the process has not yet been fully elucidated, it is believed that Gram-negative organisms possess a non-α, non-β receptor with a unique configuration for catecholamines which gives them a unique advantage in overwhelming a host's defensive mechanisms. During sepsis or related conditions, adrenal and sympathetic stimulation increase the level of circulating catecholamines in order to enhance cardiac and metabolic activity in the host. The activity of Gram-negative microorganisms under these conditions does not appear to be a typical dose response. Although not fully elucidated, it presently appears that in addition to possession of a receptor for some or all of these catecholamines, these organisms emit lipopolysaccharides which block the host's α- and β-adrenergic receptors. Thus, they prevent the re-uptake of these circulating compounds by the host to ensure that they will be able to exploit them instead.

To further substantiate the claim that a novel receptor is involved in the augmentation of growth in the presence of catecholamines, studies were repeated with the Gram-negative bacterium *Y. enterocolitica*. Table 2 demonstrates that in this bacterium, the administration of both α- and β-adrenergic receptor agonists produce no effect, yet in *E. coli* they produce enhancement of growth. Thus, *Y. enterocolitica* is more selective in its use of catecholamines. In particular, an initial inoculum of 130 CFU per well was treated with (+)-octopamine (an α-agonist), (−)-isoproterenol (a β-agonist), (+)-isoproterenol (an inactive enantiomer), and (−)-ephedrine (a dual α-, β-agonist). The incubation period was 36 hours.

INDUSTRIAL APPLICATIONS

The heretofore described effect of including catecholamines in basal culture medium for Gram-negative bacteria has important industrial ramifications. For example, the inclusion of norepinephrine in a culture of *E. coli* grown in a lactose broth was found to substantially increase the yield of glucose. FIG. 15 indicates the results of standard commercial glucose assays 24 hours after inoculation of lactose broth with *E. coli*. Thus, on a commercial scale, the proliferation of *E. coli* in the presence of norepinephrine may be exploited to produce increased yields of glucose. Similar processes with slight variation in starting materials, and according to known methods, will increase the yield of other commercially valuable products such as ethanol.

FIG. 6 demonstrates expression of β-galactosidase activity in a culture of *E. coli*. Although total expression of β-galactosidase activity is increased, actual activity per organism is suppressed. This indicates alteration of this operon and activation of genes which allow the protein to be expressed in *E. coli* is modulated in the presence of norepinephrine. Thus, this provides another example of a significant enhancement in the production of commercially viable products which may be attained by the inclusion of catecholamines, such as norepinephrine, in the appropriate culture medium.

Yet another industrial application of the method of the present invention involves clinical diagnosis of bacterial infections. I have found that current culturing techniques sometimes fail to disclose the presence of such infection when these microbes are in a phase of low concentration. Such a test will be inappropriately designated as negative, despite the presence of a low concentration of infectious agent. Thus, the inclusion of defined quantities of catecholamines in laboratory diagnostic media will augment growth, as demonstrated in FIGS. 3 and 5. This may aid in the recovery, subsequent identification and quantitation of bacterial disease during clinical diagnosis. Consequently, this will also avoid false negatives in clinical reporting.

Similarly, when biomass degradation is desired, bacterial growth could be significantly increased by the appropriate inclusion of catecholamines. In this manner, subsequent usage of the biomass is enhanced.

One skilled in the art will also recognize that the addition of at least one catecholamine to basal culture medium is beneficial to suppress unwanted growth of susceptible organisms in some industrial applications.

In addition to the augmentation of activity of commercially available products, the addition of catecholamines to basal culture medium and further study may lead to the identification of gene regulating mechanisms for these processes. The subsequent engineering of bacteria with enhanced or altered catecholamine gene regulation capabilities has many industrial applications.

FIGS. 17–20 demonstrate that the effect of norepinephrine as described herein is receptor mediated, and that the receptor involved is a new type of receptor that is not one of the presently known receptors, e.g. $\alpha_1$, $\alpha_2$, $\beta_1$, or $\beta_2$. These figures were obtained using widely accepted methods of neurotransmitter receptor analysis, including methods described in *Methods of Neurotransmitter Receptor Analysis*, Yamamura H. I., S. J. Enna, and M. J. Kuhar, Eds., New York: Raven Press, 1990. According to these accepted methods, these figures satisfy the accepted criteria for identification of a novel receptor.

FIG. 17 provides a competition/displacement curve for $^3$H-norepinephrine, in which the log of the concentration of cold norepinephrine is plotted on the abscissa and the total amount of bound $^3$H-norepinephrine (DPM) is plotted on the ordinate. Zero concentration for cold norepinephrine is represented by a box, whereas the presence of cold norepinephrine is indicated by circles. The resultant curve demonstrates that once $^3$H-norepinephrine has been bound to its receptor on *E. coli*, the addition of increasing amounts of cold norepinephrine results in displacement of the $^3$H-norepinephrine from the receptor. Because displacement is indicated, this plot provides further evidence that the phenomenon is receptor-mediated.

FIG. 18 provides a saturation curve for $^3$H-norepinephrine. Bound radioligand is presented on the ordinate and free radioligand is presented on the abscissa, as obtained from a mixture of free radioligand and cold norepinephrine. Thus, nonspecific binding (NSB), specific binding (SB), and total binding (TB) are plotted as a function of free radioligand concentration. The curves presented in FIG. 18 are analogous to those predicted for any receptor mediated process, wherein nonspecific binding appears as an essentially straight line, and is essentially parallel to the high concentration region of the curve for total binding of radioligand. Predictably, the specific binding curve tends to saturate (level off) at high radioligand concentration.

FIGS. 19A through 19C provide competition/displacement curves for the binding of *E. Coli*, grown in commercially available nutrient broth. In these curves, known antagonists for the known adrenergic receptors are applied to cultures killed by sodium azide, to investigate if the binding of catecholamines is through one of the known $\alpha_1$, $\alpha_2$, or $\beta$-adrenergic receptors. The value for zero concentration of cold norepinephrine is represented by a box, whereas the presence of cold norepinephrine is indicated by circles. Specifically, FIG. 19A demonstrates that the addition of $^3$H-prazosin, a known $\alpha_1$ receptor antagonist, does not result in any binding that can be displaced by the addition of cold norepinephrine. If the receptor was of a known $\alpha_1$ subtype, then a competition/displacement curve similar to that shown for FIG. 17 would have been obtained. FIG. 19B demonstrates that the addition of $^3$H-rauwolscine, a known $\alpha_2$ receptor antagonist, does not result in any binding that can be displaced by the addition of cold norepinephrine. If the receptor was of a known $\alpha_2$ subtype, then a competition/displacement curve also similar to that shown for FIG. 17 would have been obtained. FIG. 19C demonstrates that the addition of $^3$H-dihydroalprenolol, a known $\beta_1$ and $\beta_2$ receptor antagonist does not result in any binding that can be displaced by the addition of cold norepinephrine. If the receptor was of a known $\beta$ subtype, then a competition/displacement curve similar to that shown for FIG. 17 would have been obtained.

In summary, these adrenergic blocking agents are known to effectively bind their respective known receptors, yet the competition/displacement curves did not reveal the presence of any of the known $\alpha_1$, $\alpha_2$ or $\beta$ receptors. When this information is combined with that provided in FIGS. 1 through 18, it is surprisingly concluded that a previously unknown receptor is mediating this process.

FIG. 20 provides a tissue dependency curve for *E. coli*. As may be predicted for a receptor-mediated process, specific binding (SB) to the novel receptor is proportional to tissue (bacterial) concentration at low levels, and counts of $^3$H-norepinephrine specifically bound to its receptor on the bacteria plateau at high concentrations of bacteria when high numbers of receptors are present. In this plot of bacteria:ligand concentration dependence, specific binding (SB), as indicated by DPM, is presented on the ordinate and bacterial concentration, in CFU/ml, is presented on the abscissa.

Although FIGS. 17–20 demonstrate the specificity of this novel receptor for the catecholamines, it does not preclude that differences in receptor number (or density), as well as receptor affinity, may differ among various infectious agents. Further, my preliminary findings indicate that the density and affinity of the receptor for a given infectious agent may differ as a function of the medium or nutritive environment in which the infectious agent is grown. For example, culture of the gram-negative bacterium *Escherichia coli* in a serum-containing medium results in a catecholamine receptor density and affinity which is higher than when *E. coli* is cultured in a nutrient broth of standard microbiological medium not containing serum.

To substantiate my assertion that these findings indicate a receptor-mediated process, I conducted further experiments to test stereoselectivity and demonstrate that a nutrient-based theory will not similarly account for the detected augmentation in growth. Tested, pure (+)-norepinephrine was applied to cultures of *Y. enterocolitica* and my results indicate that the nonphysiological enantiomer did not augment growth to the degree that the active enantiomer, (−)-norepinephrine, did.

Because it has, thus, been demonstrated that the norepinephrine-induced augmentation of growth in gram-negative bacteria is based upon binding to a previously unknown receptor, it is useful to develop a method of binding this receptor for the purpose of enhancement or suppression of bacterial concentrations. In use, when it is desired to augment a population of gram-negative bacteria, the inclusion of a compound known to bind this receptor, such as norepinephrine, will produce the desired result.

The method of affecting the rate of proliferation of living organisms or vectors, such as bacteria, may be effected by the introduction of a compound, such as a known agonist or antagonist, which will specifically bind with the novel receptor demonstrated in FIGS. 17 through 19. In a living system, an initial assessment of a need to modify the level of presence of a neurotransmitter chemical, such as norepinephrine, is performed. Such an assessment may be made by incubating the organism or vector, as shown at Block 1, then evaluating the need to modify its population level, as shown at Block 2. The result of this assessment determines the antimicrobial agent and treatment protocol which will be administered, as at Block 3. In the clinical setting, this agent will be selected upon proper identification of a pathogen, typically by culturing. In a state of stress, increased levels of norepinephrine are released by a host mammalian organism. Because, as demonstrated herein, certain gram-negative pathogens have been identified as possessing a novel receptor for circulating catecholamines, and because growth is augmented in the presence of these compounds, it is desirable to block this receptor by administration of a suitable agent, since it is not possible, or if possible, not practical, to block the host organism's release of these compounds. Blocking this novel receptor in the presence of an abundance of such compounds ensures that norepinephrine-enhanced growth will be suppressed.

Alternatively, as described in reference to FIGS. 15 and 16, it is desirable in some applications to increase the population of a microbe such as E. coli., to obtain a by-product of its growth for commercial use. This may be accomplished on an industrial scale by including a catecholamine, such as norepinephrine, in the culture broth and insuring that this compound remains available as the population grows as at Blocks 4 and 5. For example, populations of E. coli grown in a lactose broth feature a substantially increased yield of glucose when norepinephrine is added to the medium. The method involved in obtaining this result includes the steps of determining the quantity of neurotransmitter substance required to produce a threshold effect on the rate of proliferation of the E. coli, adjusting the broth concentration of this neurotransmitter to this level, then assessing the efficacy of the concentration. If the concentration is not optimal, as at 6, then it is adjusted upwards or downwards until the desired enhancement in glucose yield is obtained, as at 7, as a result of the stimulating effect of the presence of the neurotransmitter. The product may then be harvested, as at Block 8.

As described herein, the living organisms or vectors which possess the genetic complement enabling possession of the novel receptor described herein include vertebrates, invertebrates, unicellular animals, multicellular animals, living tissue, unicellular plants, multicellular plants, and phages. Although described in reference to gram negative bacteria, this method has particular applicability to the control of proliferation of all infectious agents, including mycobacteria and viruses.

Finally, it has been documented that certain plants contain large amounts of catecholamines. Since it has also been documented that the presence or absence of certain bacteria may repress or enhance growth processes in these plants, it is industrially significant that these bacteria thrive or are repressed in the presence of catecholamines.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices and that various modifications, both as to equipment details and operating procedures, can be accomplished without departing from the scope of the invention itself.

What is claimed is:

1. A method of suppressing the growth of Gram-positive bacteria in a host medium, said host medium being selected from the group consisting of in vitro and cell cultures, said method comprising the introduction of an effective amount of a catecholamine to the host medium to act directly on the growth of Gram-positive bacteria.

2. A method as claimed in claim 1 wherein the catecholamine is selected from epinephrine and norepinephrine.

* * * * *